(12) United States Patent
Botti et al.

(10) Patent No.: US 9,445,992 B2
(45) Date of Patent: Sep. 20, 2016

(54) MUCOSAL DELIVERY COMPOSITIONS COMPRISING A PEPTIDE COMPLEXED WITH A CROWN COMPOUND AND/OR A COUNTER ION

(75) Inventors: Paolo Botti, Vessy/Geneva (CH); Sylvie Tchertchian, Monnetier-Mornex (FR)

(73) Assignee: ARISGEN SA (CH)

( * ) Notice: Subject to any disclaimer, the term of this patent is extended or adjusted under 35 U.S.C. 154(b) by 0 days.

(21) Appl. No.: 13/512,001

(22) PCT Filed: Nov. 25, 2010

(86) PCT No.: PCT/EP2010/068257
§ 371 (c)(1),
(2), (4) Date: Aug. 16, 2012

(87) PCT Pub. No.: WO2011/064316
PCT Pub. Date: Jun. 3, 2011

(65) Prior Publication Data
US 2012/0302502 A1 Nov. 29, 2012

Related U.S. Application Data

(60) Provisional application No. 61/264,324, filed on Nov. 25, 2009.

(51) Int. Cl.

| | |
|---|---|
| A61K 38/02 | (2006.01) |
| C07K 2/00 | (2006.01) |
| A61K 38/22 | (2006.01) |
| A61K 9/00 | (2006.01) |
| A61K 9/12 | (2006.01) |
| A61K 38/26 | (2006.01) |
| A61K 47/22 | (2006.01) |
| A61K 47/48 | (2006.01) |

(52) U.S. Cl.
CPC .............. *A61K 9/006* (2013.01); *A61K 9/12* (2013.01); *A61K 38/02* (2013.01); *A61K 38/26* (2013.01); *A61K 47/22* (2013.01); *A61K 47/48061* (2013.01)

(58) Field of Classification Search
None
See application file for complete search history.

(56) References Cited

U.S. PATENT DOCUMENTS

| | | | |
|---|---|---|---|
| 2003/0171259 A1 | 9/2003 | Modi | |
| 2009/0220452 A1* | 9/2009 | Botti | 424/85.2 |
| 2010/0137188 A1* | 6/2010 | Botti | 514/3 |

FOREIGN PATENT DOCUMENTS

| | | |
|---|---|---|
| CN | 1287486 A | 3/2001 |
| CN | 101312986 A | 11/2008 |
| CN | 101674843 A | 3/2010 |
| EP | 0 136 728 A2 | 4/1985 |
| EP | 1 338 272 A1 | 8/2003 |
| EP | 1 972 332 A1 | 9/2008 |
| WO | 2008/037484 A2 | 4/2008 |
| WO | 2011/064300 A1 | 6/2011 |

OTHER PUBLICATIONS

Pathan et al., Recent Patents on Drug Delivery & Formulation (2008) 2, 177-188.*
Graf et al., Electrophoresis (2005) 26, 2409-2417.*
Sigma-Aldrich catalog retrieved from http://www.sigmaaldrich.com/life-science/metabolomics/enzyme-explorer/analytical-enzymes/chymotrypsin.html.*
Mascagni et al., J. Chem. Soc. Perkin Trans. II (1987) 323-327.*
Veuillez et al., European Journal of Pharmaceutics and Biopharmaceutics (2001) 51, 93-109.*
International Application No. PCT/EP2010/068257, International Search Report and Written Opinion of the International Searching Authority dated Nov. 11, 2011.
Botti, P, et al., The Use of Crown Ethers in Peptide Chemistry IV. Solid Phase Syntehsis of Peptides Usig Peptide Fragents Nalpha Protected with 18-Crown-6, Tetrahedron, 51(18):5447-5458 (1995).

* cited by examiner

*Primary Examiner* — Marcela M Cordero Garcia
*Assistant Examiner* — Catherine Mader
(74) *Attorney, Agent, or Firm* — Pillsbury Winthrop Shaw Pittman LLP

(57) ABSTRACT

Compositions and methods are provided for mucosal delivery of peptides. The compositions include a stably hydrated peptide active agent complexed with a crown compound and/or a counter ion solubilized in a non-aqueous hydrophobic vehicle at a pH different from the pI of the peptide active agent. The methods include administering to a subject an effective amount of a composition of the disclosure. Other aspects include methods for the manufacture of the compositions of the disclosure. Also provided are compositions and kits that find use in practicing embodiments of the disclosure. The methods and compositions find use in a variety of applications, including the treatment of a variety of different disease conditions.

57 Claims, 4 Drawing Sheets

SEQUENCE LISTING

```
<160> NUMBER OF SEQ ID NOS: 1

<210> SEQ ID NO 1
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: AMIDATION

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

```
Ser Gly Ala Pro Pro Pro Ser
    35
```

MUCOSAL DELIVERY COMPOSITIONS COMPRISING A PEPTIDE COMPLEXED WITH A CROWN COMPOUND AND/OR A COUNTER ION

RELATED APPLICATIONS

This application is the National Phase of International Application No. PCT/EP2010/068257, filed Nov. 25, 2010, which designated the U.S. and that International Application was published under PCT Article 21(2) in English, and claims priority to U.S. Provisional Application No. 61/264,324, filed Nov. 25, 2009, all of which applications are incorporated herein by reference in their entirety.

TECHNICAL FIELD

The disclosure relates to compositions and methods for mucosal delivery of peptides, particularly oral mucosal delivery for absorption through oral mucosal membranes.

INTRODUCTION

Peptide-based drugs are typically delivered by injection, since oral delivery by ingestion is often hindered by poor intrinsic permeability and degradation in the gastrointestinal (GI) tract. Nevertheless, the potential therapeutic benefit remains significant, including ease of use and better overall patient compliance.

Mucosal delivery of peptides into the blood stream of a host across various mucosal membranes, such as found in the GI tract, lung, nasal cavity and oral cavity, is possible for a number of peptides and peptide formulations. However, the fraction of an administered dose of unchanged peptide that reaches the systemic circulation (i.e., bioavailability) normally varies depending on the particular route of delivery, peptide and formulation. Thus, the non-invasive delivery of peptide drugs by mucosal routes offers significant flexibility.

For example, delivery of drugs via oral mucosa provides direct access to the systemic circulation through the internal jugular vein, allowing them to bypass the gut and hepatic first-pass metabolism, and enter the bloodstream for rapid on-set of effect. As such, the mucosal lining in the oral cavity represents a promising topical route for the delivery of large therapeutic molecules such as insulin, interferons, and interleukins (Veuillez et al., Eur. J. Pharm. Biopharm. (2001) 51:93-109; and Sudhakar et al., J. Control. Release (2006) 114:15-40; and Amin et al., Drug Delivery Technology (2007) 7(3) 48, 50-55).

One drawback of oral mucosal delivery of larger molecules is their poor overall bioavailability. In this regard, various approaches have been explored to improve the oral mucosal absorption of peptides, including use of absorption enhancers to increase mucosal membrane permeability and/or the addition of enzyme inhibitors to increase drug stability. Many substances can function as absorption enhancers, one of the most popular being detergents such as bile acid salts, sodium lauryl sulfate, and the like based on intercellular lipid solubilization (Aungst et al., Intl. J. Pharmaceutics (1989) 53(3):227-35; Druker, D. J., Curr Pharm Design (2001) 7(14):1399-1412; and Berstein, G., Drug Development Res. (2006) 67(7):597-599). Cyclic compounds such as crowns have also been used (WO 08/037,484).

Reservoir-type devices filled with drug, along with cholate as a penetration enhancer, have been reported for buccal delivery of insulin (U.S. Pat. Nos. 4,671,953; 4,863,737; 5,122,127; and 5,132,114). Lipid vesicles composed of soybean phosphatidylcholine, cholesterol, and sodium deoxycholate, has been reported to enhance insulin bioavailability as well (Yang et al., Chem. Pharm. Bull. (2002) 50:749-753). Gels composed of Pluronic F-127 (PF-127) containing insulin and unsaturated fatty acids, such as oleic acid (18:1), eicosapentaenoic acid (20:5), or docosahexaenoic acid (22:6) have been reported (Morishita et al., Int. J. Pharm. (2001) 212:289-293). The absorption enhancer lysalbinic acid, which is a product of the alkaline hydrolysis of egg albumin and a mild detergent, also has been reported for molecules such as α-interferon and insulin (Starokadomskyy et al., Int. J. Pharm. (2006) 308:149-154). Various delivery systems have been reported for buccal delivery of glucagon-like insulinotropic peptide (GLP-1) (U.S. Pat. Nos. 5,863,555 and 5,766,620).

A variety of mucoadhesive dosage forms also have been reported to increase resident time of the delivery system in the oral cavity (Ishida et al., Chem. Pharm. Bull. (1981) 29:810-816; and Senel et al., Curr. Pharm. Biotechnol. (2001) 2:175-186), including, for example, pelleted mucoadhesive polymeric nanoparticles (Venugopalan et al., Pharmazie (2001) 56:217-219), and mucoadhesive tablets (Hosny et al., Boll. Chim. Farm. (2002) 141:210-217).

Mucosal dosage forms employing various solvents have also been reported, such as insulin with soybean lecithin and propanediol (Xu et al., Pharmacol. Res. (2002) 46:459-467), and buccal aerosol sprays and capsules using non-polar solvent (U.S. Pat. No. 5,955,098). Pulmonary delivery formulations of a solution or suspension of various organic solvents have been reported, for example, where the solvent is a class 3 residual solvent such as ethanol, acetone, ethyl acetate, tetrahydrofuran, ethyl ether, and propanol (U.S. Pat. No. 6,660,715).

Despite advances, mucosal delivery systems often include absorption enhancing formulations that exhibit side effects, such as causing irritation of the various mucosal linings in the mouth or airways. Another problem is the repugnant taste of many compositions, particularly for bile salts, pointing to likely issues with patient acceptance and compliance. A different issue relates to the volume required for delivering a sufficient amount of an active peptide ingredient for biological effect, storage stability, and reproducibility.

Such deficiencies point to an unmet need for compositions and methods for administering peptides that are stable, well tolerated, provide enhanced and reliable mucosal delivery, particularly oral mucosal delivery, and suitable for treatment of diseases and other adverse conditions in mammalian subjects. A related need exists for methods and compositions that provide efficient delivery of larger drugs such as peptides via one or more mucosal routes in therapeutic amounts, which are fast acting, easily administered, have limited adverse side effects such as mucosal irritation or tissue damage, and reproducible. There is also a need for non-aqueous pharmaceutical and diagnostic compositions of peptides which have improved stability. An additional need relates to the manufacture of such materials, and compositions for the same. The present disclosure addresses these and other needs.

Relevant Literature

Various peptides, uses, formulations and delivery routes and systems are reported in the following: U.S. Pat. Nos. 4,671,953; 4,863,737; 5,122,127; 5,132,114; 5,346,701; 5,424,286; 5,545,618; 5,614,492; 5,631,224; 5,766,620; 5,869,082; 6,268,343; 6,312,665; 6,375,975; 6,436,367; 6,451,286; 6,458,924; 6,660,715; 6,676,931; 6,770,625; 6,867,183; 6,902,744; 6,969,508; 6,977,070; 6,998,110;

7,030,082; 7,070,799; 7,169,410; 7,196,059; and International Patent Application Nos.: WO 9715297; WO/1999/016417; WO/2002/064115; WO/2003/024425; WO/2004/105790; WO/2006/025882; WO/2006/037811; WO/2006/103657; WO/2006/105615; WO/2006/127361; WO/2006/135930; WO/2007/014391; WO/2007/065156; WO/2007/067964; WO/2007/083146; WO/2007/121256; WO/2007/146448; WO/2008/037484; WO/2008/145728; WO/2008/145732; and WO/2008/016729;

Various references discuss alternatives to subcutaneous injection (s.c.) of peptides and uses, including peroral, intra oral (buccal/sublingual), rectal, transdermal, intra nasal, and intra pulmonary delivery routes: Touitou, E., *J. Controlled Rel* (1992) 21:139-144; Amin et al., *Drug Delivery Technology* (2007) 7(3) 48, 50-55; Aungst et al., *Pharmaceutical Research* (1988) 5(5):305-308; Aungst et al., *Intl. J. Pharmaceutics* (1989) 53(3):227-35; Berstein, G., *Drug Development Res.* (2006) 67(7):597-599; Druker, D. J., *Curr Pharm Design* (2001) 7(14):1399-1412; Hosny et al., *Bollettino Chimico Farmaceutico* (2002), 141(3):210-217; Khafagy et al., *Advanced Drug Delivery Reviews* (2007) 59(15):1521-1546; Lassmann-Vague et al., *Diabetes & Metabolism* (2006) 32(5, Pt 2):513-522; Morishita et al., *Intl. J. Pharmaceutics* (2001) 212(2):289-293; Patel et al., *Drug Delivery Technology* (2006) 6(3)48-60; Pillion et al., *J. Pharm. Sci.* (1995) 84(11):1276-1279; Portero et al, *Carbohydrate Polymers* (2007) 68(4):617-625; Pozzilli et al., *Metabolism, Clinical and Experimental* (2005) 54(7): 930-934; Owens, D. R., *Nature Reviews Drug Discovery* (2002) 1(7):529-540; Rossi et al., *American J. Drug Delivery* (2005) 3(4):215-225; Sadrzadeh et al., *J. Pharm Sci* (2007) 96(8):1925-1954; Starokadomskyy et al., *Intl. J. Pharmaceutics* (2006) 308(1-2):149-154; Xu et al., *Pharmacological Research* (2002) 46(5:459-467; Yang et al., *S.T.P. Pharm. Sciences* (2001) 11(6):415-419; Yang et al., *Chemical & Pharmaceutical Bulletin* (2002) 50(6):749-753;

Klibanov et al. (1995 supra) reported on lyophilization of various biomolecules from aqueous solutions of different pH's and their subsequent solubility in methanol and ethanol.

US 2006/0178304 discloses lyophilization of various glucagon-like peptides from aqueous solutions or suspensions of different pH's and their subsequent solubility in aqueous solutions or suspensions.

SUMMARY

Compositions and methods related to mucosal delivery of peptide active agents are provided. The mucosal delivery compositions include an effective amount of a stably hydrated peptide active agent complexed with a crown compound and/or a counter ion solubilized in a non-aqueous hydrophobic vehicle at a pH different from the isoelectric point of the peptide active agent. Also provided are compositions that include a preformed peptide complex comprising a stably hydrated peptide active agent complexed with a crown compound and/or a counter ion, wherein the performed peptide complex is dried from a solution or suspension having a pH different, optionally remote, from the isoelectric point of the peptide active agent. Additional compositions include an effective amount of a stably hydrated peptide active agent complexed with a counter ion solubilized in a non-aqueous hydrophobic vehicle at a pH different from the isoelectric point of the peptide active agent, wherein the stably hydrated peptide active agent complexed with a counter ion is dried from a solution or suspension having a pH different, optionally remote, from the isoelectric point of the peptide active agent, and wherein the non-aqueous hydrophobic vehicle in many embodiments comprises at least one acylglycerol and at least one organic solvent and/or lipid. Further provided are pharmaceutical and/or diagnostic preparations of the subject compositions.

Also provided are methods of production. In certain embodiments, the method comprises forming a soluble peptide complex in a non-aqueous hydrophobic vehicle at a pH different from the isoelectric point of the peptide active agent, the peptide complex comprising an effective amount of a stably hydrated peptide active agent complexed with a crown compound and a counter ion. A method is also provided for production of a preformed peptide complex comprising a stably hydrated peptide active agent complexed with a crown compound and a counter ion, the method involving (i) forming the peptide complex in a solution or suspension having a pH different, optionally remote, from the isoelectric point of the peptide active agent, and (ii) drying the peptide complex from the solution or suspension under conditions that retain a sufficient amount of water in association with the peptide active agent to stabilize the peptide active agent, whereby the preformed peptide complex is produced. Another method is provided that involves solubilizing an effective amount of a stably hydrated peptide active agent complexed with a counter ion in a non-aqueous hydrophobic vehicle at a pH different from the isoelectric point of the peptide active agent, wherein the stably hydrated peptide active agent complexed with a counter ion is dried from a solution or suspension having a pH different, optionally remote, from the isoelectric point of the peptide active agent, and wherein the non-aqueous hydrophobic vehicle in many embodiments comprises at least one acylglycerol and at least one organic solvent and/or lipid.

Methods for the mucosal delivery of an effective amount of a peptide active agent to a host in need thereof are also provided. The method involves administering to a mucosal membrane of the host an effective amount of a mucosal delivery composition of the disclosure, wherein the administering delivers an effective amount of the peptide active agent into the blood stream of the host. In a featured embodiment, the mucosal delivery composition is an oral mucosal delivery composition, and the mucosal membrane is an oral mucosal membrane.

Further provided are kits that find use in practicing the subject methods. In certain embodiments, the kit comprises an effective amount of a mucosal delivery composition of the disclosure, and/or components thereof each individually provided in various combinations in the kit in effective amounts capable of forming the mucosal delivery composition upon combination.

The subject methods and compositions find use in a wide range of different applications, including the treatment of a variety of different disease conditions. An exemplary application illustrating a significant advantage of the methods and compositions disclosed herein is the enhanced mucosal delivery of peptides, and in particular, reliably reproducible mucosal delivery imparted by formation and use of a stably hydrated form of the peptide active agent maintained in the peptide complex and non-aqueous hydrophobic vehicle. The subject compositions and methods are particularly useful for mucosal delivery of peptide hormones, such as glucagon-like peptide-1 and analogs thereof exemplified by liraglutide and exendin-4 (exenatide) that can affect blood glucose levels in vivo for treatment of diabetes, obesity, and related disorders. Thus, in certain embodiments, specific compositions and methods are provided for mucosal delivery of a peptide active agent for treatment of diabetes, obesity, and related disorders.

Other features of the disclosure are described herein, and will also be readily apparent to the ordinarily skilled artisan upon reading the present disclosure.

DEFINITIONS

Figure 1:
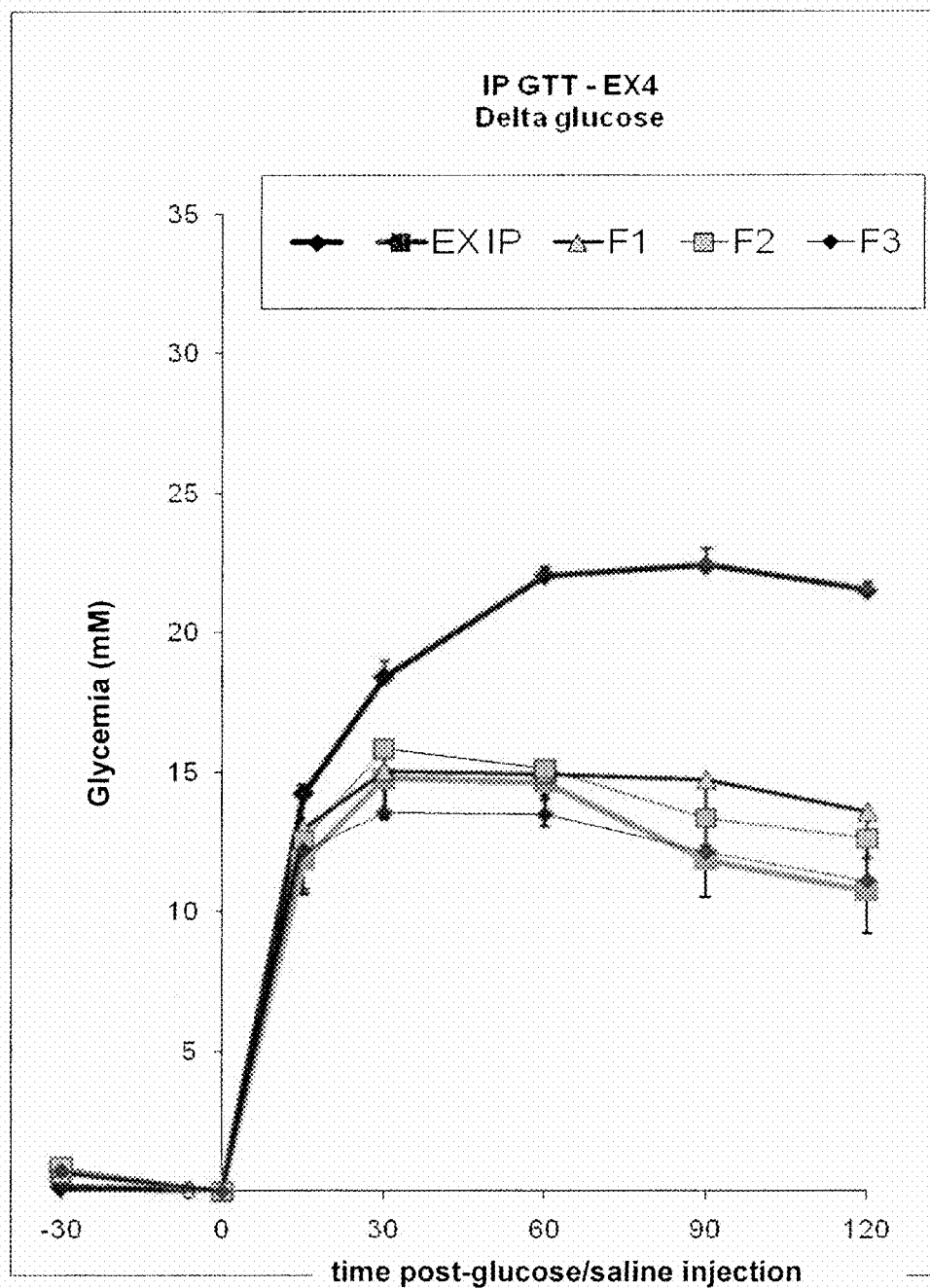
FIG. 1 depicts a set of results demonstrating the effect of the type of counter ion on sublingual delivery of exendin-4 in a representative mucosal delivery composition, and reduction of glucose levels in mice as measured by intraperitoneal glucose tolerance tests (IPGTT).

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

"Amino acid" refers to any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form, as well as analogues/derivatives thereof. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine). Thus, the amino acids includes protected or modified amino acids, such as acylated amino acids, amidated amino acids and the like.

"Analogue" or "derivative" refers to without limitation any compound which has a structure derived from the structure of the compounds of the present disclosure and whose structure is sufficiently similar to those disclosed herein and based upon that similarity, would be expected, by one skilled in the art, to exhibit the same or similar activities and utilities as the claimed and/or referenced compounds.

"Buccal mucosa" refers to the membrane lining the inner wall of the cheek.

"Charge complexing agent" refers to a compound that forms a non-covalent complex with an ion, atom or ionizable functional group of a molecule, where the complex represents a reversible association of the complexing agent with one or more ions, atoms, or molecules through non-covalent chemical bonds.

"Complexed" or "charge complex" refers to a reversible association of a charge complexing agent such as a crown compound that forms a non-covalent complex with an ion, atom or ionizable functional group of a molecule through non-covalent chemical bonds. As used herein, the term complexed or charge complex is not confined to salt or metal ions bound to a complexing agent. It relates in general to complexes between a complexing agent and an ion or ionic group on a peptide, particularly a cation or cationic group on a peptide.

"Crown compound" refers to macrocyclic polydentate compounds, usually uncharged, in which three or more coordinating ring atoms (usually oxygen or nitrogen) are or may become suitably close for easy formation of chelate complexes with cationic species (excludes planar analogues, such as porphyrins). See for example: M. Hiraoka, Crown Compounds: their Characteristics and Applications, Elsevier Science Publishers, 1982; and E. Weber and F. Vögtle, Inorg. Chim. Acta (1980) 45:L65-L67.

"Dried peptide" refers to a peptide dried by a process, such as lyophilization, spray drying, centrifugal evaporation, and air drying, and which contains residual water in association with the peptide. The dried peptide is typically a powder or residue that can have the appearance of a dry powder, particulate, or residue material, including an oily or moistened residue appearance. By contrast, an "anhydrous peptide" contains essentially no water. See for example, lyophilization (e.g., Williams and Polli (1984) J. Parenteral Sci. Technol. 38:48-59); spray drying (e.g., Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20); air drying (e.g., Carpenter and Crowe (1988) Cryobiology 25:459-470; and Roser (1991) Biopharm. 4:47-53); and centrifugal evaporation (e.g., www.genevac.com).

"Effective" means adequate to accomplish a desired, expected, or intended result. For example, the term "effective amount" or "pharmaceutically effective amount" as provided herein is intended to mean a non-lethal but sufficient amount of the compound to provide the desired utility. For instance, for decreasing blood glucose levels in a host, the effective amount is the amount which elicits a useful response (e.g., reduction of blood glucose levels below control level, or to provide for a clinically meaningful reduction in blood glucose levels). As will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

"Ionizable functional group" refers to a group on an amino acid of a peptide capable of donating or accepting a charge at a pH different from the group's pKa.

"Mucosal delivery" refers to application of an active agent (such as a drug) to one or more mucosal membranes of the gastrointestinal tract (GI), rectum, vagina, lung, nasal cavity, or oral cavity, including buccal (cheek), sublingual (under tongue), lips, gums, palates, and tongue, and passage of the active agent through the membranes covering these places and its entry into the bloodstream.

"Mucosal delivery composition" refers to a drug delivery composition or system capable of mucosal delivery of an active agent.

"Peptide" refers to a polyamino acid containing up to 2, 5, 10, 20, 30, 40, 50, 75, 100 or about 200 amino acid residues, which can include coded and non-coded amino acids, chemically or biochemically modified or derivatized amino acids, linear, branched or cyclic peptide, and peptides having modified backbones. Sometimes referred to as polypeptide or protein, which may be used interchangeably herein. For example, includes peptides which comprise one or more non-naturally occurring amino acids such as beta-alanine, alpha-amino butyric acid, gamma-amino butyric acid, alpha-amino isobutyric acid, norvaline, norleucine, ornithine, homoserine and hydroxyproline. For example, includes peptides in which reactive groups are modified, such as the N- and C-terminus of a peptide may be chemically modified by various labeling agents, polymers such as polyethylene glycol, lipids, carbohydrates and the like, blocked by protecting groups, and the like, as well as those bearing biological modifications, such as post-translational modifications.

"Peptide active agent" refers to a biologically active peptide or an analogue/derivative thereof, including pharmaceutically acceptable salts, solvates, hydrates, and prodrug forms thereof.

"Percent solubility value" refers to the equilibrium solubility limit or maximum solubility of a molecule in a solvent or solvent system at usual room temperature, expressed as the weight percent of the molecule in the composition.

"Permeability-enhancing lipid" refers to charged or neutral hydrophobic or amphiphilic small molecules that may be either solid or liquid at normal room temperature, depending on their structure and composition, may be saturated or unsaturated, branched or linear, and are capable of enhancing the permeability of mucosal membranes to absorption of peptides. May include fats, waxes, sterols, fat-soluble vitamins (such as vitamins A, D, E and K), monoglycerides, diglycerides, phospholipids, and others, such as oleic acid, sterols such as cholesterol, triglycerides composed of oleoyl, stearoyl, and palmitoyl chains attached to a glycerol backbone, phospholipids such as phosphatidylcholine, and the like. A subset of the permeability-enhancing lipids is a "permeability-enhancing fatty acid," which refers to aliphatic carboxylic acids that may be saturated or unsaturated, branched or linear, and are capable of enhancing the permeability of mucosal membranes to absorption of peptides.

"Oral mucosal delivery" refers to application of an active agent (such as a drug) to one or more mucosal membranes of the oral cavity, including buccal (cheek), sublingual (under tongue), lips, gums, palates, and tongue, and passage of the active agent through the membranes covering these places and its entry into the bloodstream.

"Oral mucosal delivery vehicle" refers to a drug delivery system capable of oral mucosal delivery of an active agent.

"Solvation" refers to the interaction of a solute, such as a peptide, with a solvent, such as an aqueous, organic, or an aqueous organic solution, which leads to stabilization of the solute in the solvent.

"Solubility" refers to the dynamic equilibrium state achieved when the rate of dissolution equals the rate of precipitation. The extent of the solubility of a substance in a specific solvent is measured as the saturation concentration where adding more solute does not increase the concentration of the solution.

"Stably hydrated peptide active agent" refers to a peptide active agent having a water content by weight and solubility in an organic or aqueous organic solvent comparable to or greater than the dried peptide active agent, and is essentially non-aggregated and unoxidized.

"Sublingual mucosa" refers to the membrane that includes the ventral surface of the tongue and the floor of the mouth.

The terms "determining," "measuring," and "assessing," and "assaying" are used interchangeably and include both quantitative and qualitative determinations.

The term "pharmaceutically acceptable" refers to a material that is not biologically or otherwise undesirable, i.e., the material is of a medically acceptable quality and composition that may be administered to an individual along with the selected active pharmaceutical ingredient without causing any undesirable biological effects or interacting in a deleterious manner with any of the other components of the pharmaceutical composition in which it is contained.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

As summarized above, the present disclosure provides compositions and methods of their preparation for mucosal delivery of peptide active agents. Also provided are kits and methods of use of the subject compositions.

The compositions include a mucosal delivery composition that comprises an effective amount of a peptide complex or a peptide salt solubilized in a non-aqueous hydrophobic vehicle. The peptide complex includes a stably hydrated peptide active agent complexed with a crown compound and/or a counter ion, and is solubilized in the non-aqueous hydrophobic vehicle at a pH different from the pI of the peptide active agent. The peptide salt includes a stably hydrated peptide active agent complexed with a counter ion, and is solubilized in the non-aqueous hydrophobic vehicle at a pH different from the pI of the peptide active agent.

In certain embodiments, the non-aqueous hydrophobic vehicle comprises at least one acylglycerol, and at least one organic solvent and/or lipid each individually present in an amount effective to (i) solubilize the peptide complex or peptide salt, and (ii) enhance mucosal delivery of the peptide active agent. Thus, the mucosal delivery composition generally includes various solubilizing agents in non-aqueous medium, such as a medium comprising an acylglycerol and an organic solvent and/or a lipid (as described in greater detail below). The mucosal delivery composition and components thereof may also include one or more additional pharmaceutically acceptable excipients, such as one or more of an non-ionic surfactant, antioxidant, buffer, preservative, and the like (as described in greater detail below).

In many embodiments, the peptide complex or the peptide salt is preformed, wherein the preformed peptide complex or preformed peptide salt is dried from a solution or suspension having a pH different, optionally remote, from the pI of the peptide active agent. In as many embodiments, the non-aqueous hydrophobic vehicle is preformed. In some embodiments, the preformed non-aqueous hydrophobic vehicle is dried from a solution or suspension having a pH different, optionally remote, from the isoelectric point of the peptide active agent. In some embodiments, the mucosal delivery composition is dried from a solution or suspension having a pH different, optionally remote, from the isoelectric point of the peptide active agent. In certain embodiments, the solution or suspension is an aqueous organic mixture. As such, further embodiments are directed to a composition comprising one or more of the preformed peptide complex, the preformed peptide salt, the preformed non-aqueous hydrophobic vehicle, and combinations thereof.

Methods of production of the subject compositions also are provided. In one embodiment, a method of producing a mucosal delivery composition is provided, the method comprising: forming a peptide complex or peptide salt dispersed in a non-aqueous hydrophobic vehicle at a pH different from the pI of the peptide active agent, the peptide complex comprising an effective amount of a stably hydrated peptide active agent complexed with a crown compound and a counter ion, the peptide salt comprising an effective amount of a stably hydrated peptide active agent complexed with a counter ion. A featured embodiment is where the peptide complex or peptide salt is solubilized at a pH different from the pI of the peptide active agent in the non-aqueous hydrophobic vehicle.

The forming step of the subject method comprises combining an effective amount of each component (or any effective combination thereof) of the desired mucosal delivery composition (i.e., combining an effective amount of components comprising the stably hydrated peptide active agent, the crown compound, the counter ion, and the non-aqueous hydrophobic vehicle for mucosal delivery compositions in which a crown compound is included, or combining an effective amount of the components comprising the stably hydrated peptide active agent, the counter ion, and the non-aqueous hydrophobic vehicle for mucosal delivery compositions in which a crown compound is absent).

For example, in certain embodiments, the forming step of the subject method comprises combining an effective amount of (i) a first composition comprising the non-aqueous hydrophobic vehicle, and (ii) a second composition comprising the peptide complex or the peptide salt. In other embodiments, for instance, the forming step of the subject method comprises combining an effective amount of (i) a first composition comprising the non-aqueous hydrophobic vehicle and the peptide salt, and (ii) a second composition comprising a crown compound.

In the subject methods of production, the peptide complex or peptide salt in many embodiments is comprised as a dried powder or residue obtainable by drying a solution or suspension, the solution or suspension comprising as components therein: (i) the peptide active agent, the crown compound, and the counter ion for forming the peptide complex, or (ii) the peptide active agent, and the counter ion for forming the peptide salt; and wherein the drying is under conditions that retain a sufficient amount of water in association with the peptide active agent to produce the peptide complex or peptide salt. In certain embodiments, the solution or suspension is at pH different, optionally remote, from the isoelectric point of the peptide active agent. In a specific embodiment, the solution or suspension is an aqueous organic solution or suspension. In particular embodiments, the peptide complex and/or the peptide salt is preformed as a dried powder or residue. A featured aspect is where one or more of the dried powder or residue comprising the peptide complex, the peptide salt, the peptide active agent, the crown compound, and/or the counter ion is soluble in the aqueous organic solution or suspension. A specific embodiment is where the dried powder or residue comprising the peptide complex, or the peptide salt is soluble in the aqueous organic solution or suspension.

Thus in many embodiments, a method of producing a mucosal delivery composition is provided that comprises:

(a) providing a first composition comprising a peptide active agent as a preformed salt that is dried from an aqueous or aqueous organic solution or suspension having a pH different, optionally remote, from the pI of the peptide active agent, the drying under conditions that retain a sufficient amount of water in association with the peptide to maintain solvation and stability of the peptide active agent; and (b) combining the preformed peptide salt of step (a) with a second composition comprising a non-aqueous hydrophobic vehicle to form the mucosal delivery composition; or (c) combining the preformed peptide salt of step (a) with a second composition comprising a non-aqueous hydrophobic vehicle and a crown compound to form the mucosal delivery composition; or (d) combining the preformed peptide salt of step (a) with a second composition comprising a crown compound in an organic or aqueous organic solution or suspension, and (i) drying the organic or aqueous organic solution or suspension to form a preformed peptide complex under conditions that retain a sufficient amount of water in association with the peptide to maintain solvation and stability of the peptide active agent; and (ii) combining the preformed peptide complex with the non-aqueous hydrophobic vehicle to form the mucosal delivery composition.

Methods are also provided for production of a preformed peptide complex and/or a preformed peptide salt, such as described above. For example, in one embodiment, the method involves (i) providing an aqueous organic solution or suspension comprising as components therein a peptide active agent, a crown compound, and a counter ion, and (ii) drying the aqueous organic solution or suspension under conditions that retain a sufficient amount of water in association with the peptide active agent to produce the peptide complex. In a related embodiment, the aqueous organic solution or suspension is at a pH different, optionally remote, from the pI of the peptide active agent.

Methods for the mucosal delivery of an effective amount of a peptide active agent to a host in need thereof are also provided. The method involves administering to a mucosal membrane of the host an effective amount of a mucosal delivery composition of the disclosure, wherein the administering delivers an effective amount of the peptide active agent into the blood stream of the host. Further provided are kits that find use in practicing the subject methods.

The mucosal delivery compositions and its components are generally non-toxic and non-irritating, and facilitate enhanced and reliably reproducible mucosal delivery of the stably peptide active agent into the blood stream of the host, relative to the non-stably hydrated peptide active agent. The subject compositions may be administered alone or as part of a drug delivery system for delivery to one or more mucosal membranes of a host, such as administration to the oral cavity of a host for oral mucosal delivery through an oral mucosal membrane, such as a buccal membrane, sublingual membrane, or both buccal and sublingual membranes. Thus, the compositions can be provided in a free form, such as a liquid, gel, foam, cream, ointment, semi-solid, or spray, or can comprise a device of determined physical form, such as tablets, patches, films, and troches.

The subject compositions and methods find use in a variety of different applications, including the treatment of a range of different disease conditions for which a given peptide active agent is indicated. An exemplary application illustrating a significant advantage of the methods and compositions of the disclosure is the effective and reliably reproducible oral mucosal delivery of peptide hormones such as insulin and incretin mimetic peptides that alter blood glucose levels in vivo for treatment of diabetes, obesity, and related disorders. As such, the subject compositions and methods represent an important advance over the prior art. In particular, a significant problem overcome by the present disclosure is the reliable and reproducible mucosal delivery of peptide active agents, among other aspects.

In further describing the subject disclosure, the subject compositions and related methods of production are described first in greater detail, followed by a review of the various pharmaceutical/diagnostic formulations and kits that may find use in the subject methods, as well as a discussion of various representative applications in which the subject compositions and methods find use.

Compositions and Methods of Production

The present disclosure is based in part on the discovery that a remarkable improvement in the mucosal delivery of peptides can be achieved by providing a mucosal delivery composition comprising an effective amount of a stably hydrated peptide active agent complexed with a crown compound and a counter ion solubilized in a non-aqueous hydrophobic vehicle at a pH different from the isoelectric point (pI) of the peptide active agent. The stably hydrated peptide active agent complexed with a crown compound and a counter ion, also referred to herein as the peptide complex, is readily prepared in situ in the non-aqueous hydrophobic vehicle or pre-formed ex situ, with the proviso that the peptide active agent is processed under conditions that retain a sufficient amount of water in association with the peptide to maintain solvation and stability of the peptide active agent.

Thus in certain embodiments, the peptide complex is prepared ex situ as a preformed peptide complex, and then combined with the non-aqueous hydrophobic vehicle. In other embodiments, the peptide complex is prepared in situ in the non-aqueous hydrophobic vehicle, for example, by combining (i) a crown compound with (ii) a non-aqueous hydrophobic vehicle comprising the stably hydrated peptide active agent in complex with a counter ion as a peptide salt, with the proviso that the peptide active agent is processed under conditions that retain a sufficient amount of water in association with the peptide to maintain solvation and stability of the peptide active agent.

The present disclosure is also based in part on the finding that a significant improvement in solubility of the peptide complex or peptide salt in a non-aqueous hydrophobic vehicle can be achieved when the peptide complex or peptide salt is dried from a solution or suspension at a pH different, optionally remote, from the pI of the peptide active agent. The mucosal delivery composition can be readily prepared in situ or ex situ utilizing such a dried peptide complex or peptide salt, with the proviso that the peptide active agent is processed under conditions that retain a sufficient amount of water in association with the peptide to maintain solvation and stability of the peptide active agent.

Thus whether the mucosal delivery composition is formed by an in situ or ex situ process as described above, reliable and reproducible mucosal delivery of the peptide active agent strongly depends on the conditions under which the composition is prepared. For example, the following process of the disclosure illustrates this point, and can be characterized as involving two basic steps.

In a first step, the peptide active agent is generally provided as a performed salt that is dried (e.g., by lyophilization or spray drying) from an aqueous or aqueous organic solution or suspension (e.g., water, water/acetonitrile mixtures) having a pH different, optionally remote, from the pI of the peptide active agent. Depending on the pH of the solution or suspension and the pI of the peptide, this step is readily employed whether the preformed salt is utilized straight from purification (e.g., HPLC using water/acetonitrile mixtures in the presence of desired counter ion, such as acetic acid) or prepared from a precursor peptide salt (e.g., peptide trifluoroacetic acid) that is subjected to desalting and counter ion exchange when a different counter ion is desired (e.g., peptide salicylic acid). Again, for desalting and counter ion exchange, aqueous or aqueous organic solutions or suspensions (e.g., water, water/acetonitrile mixtures) are employed, and the desired preformed peptide salt is eventually dried (e.g., by concentrating as a residue by centrifugal evaporation/SpeedVac, lyophilization or spray drying) from a solution or suspension having a pH different, optionally remote, from the pI of the peptide active agent, to form the desired preformed peptide salt. In each step, care is taken so that the peptide active agent is processed under conditions that retain a sufficient amount of water in association with the peptide to maintain solvation and stability of the peptide active agent.

In a second step, the mucosal delivery composition is then formed by either: (i) combining the dried preformed peptide salt of the first step with a crown compound (or without a crown compound in certain embodiments) and the non-aqueous hydrophobic vehicle to form the mucosal delivery composition; or (ii) (a) combining the dried preformed peptide salt of the first step with the crown compound in an organic or aqueous organic solution or suspension (e.g., methanol, water/methanol mixtures), (b) drying the organic or aqueous organic solution or suspension of step (ii)(b) (e.g., by concentrating as a residue in a centrifugal evaporator/SpeedVac), and then (c) combining the dried peptide material of step (ii)(b) (which comprises the preformed peptide complex) with the non-aqueous hydrophobic vehicle to form the mucosal delivery composition. In each step, care is taken so that the peptide active agent is processed under conditions that retain a sufficient amount of water in association with the peptide to maintain solvation and stability of the peptide active agent.

In certain embodiments, an effective amount of one or more stabilizing excipients and/or water is optionally added to the dried peptide salt before, during, and/or after complexation with the crown compound in an amount that maintains solvation and stability of the peptide active agent. For instance, water can be combined with and used to first dissolve the preformed peptide salt, followed by the addition of a solvent mixture such as methanol and crown compound to aid in forming and/or maintaining the stably hydrated peptide during complexation (e.g., water added such that the final water concentration in the water-solvent mixture is in a range from 0.5%-50%, more preferably about 1%-35%, often about 5%-25%, and typically about 10-15%, followed by drying to remove solvent). Water also may be optionally combined with the peptide complex prior to and/or in conjunction with its combination with the non-aqueous hydrophobic vehicle (e.g., water added to the dried peptide complex prior to combination with the non-aqueous hydrophobic vehicle such that the final water concentration in the formulation mixture is about 0.1%-10%, usually about 0.5%-5%, and typically about 1%-3%, with the proviso that the amount of water added is about or less than the amount capable of inducing unwanted phase separation of the formulation components). In another example, an effective amount of one or more stabilizing excipients may be included in one or more steps of preparing the preformed peptide salt and/or peptide complex, such as in the counter ion exchange process before, during, and/or after drying, to aid in maintaining the stably hydrated peptide (e.g., a non-ionic detergent such as beta-D-octylglucoside, a tonicity modifying agent such as a mannitol, and the like). Additional water and/or one or more stabilizing excipients may be combined in the final mucosal delivery formulation as well in an amount sufficient to maintain solvation and stability of the peptide active agent.

As such, the stably hydrated peptide active agent (alone or in complex with a crown compound and/or counter ion) is readily prepared by drying the desired peptide material from a solution or suspension at a pH different, optionally remote, from the pI of the peptide active agent, with the proviso that the peptide active agent is processed under conditions that retain a sufficient amount of water in association with the peptide to maintain solvation and stability of the peptide. The solution or suspension can be aqueous, organic, or mixtures thereof. The resultant dried peptide material (e.g., peptide alone, peptide salt, or peptide complex) can be stored for later use, and/or further processed, such as combined as above with one or more of the remaining components of the mucosal delivery composition.

While the pH range of the solution or suspension from which the peptide material is dried may overlap with the pI of the stably hydrated peptide active agent, in general, the farther away the solution or suspension's midpoint pH is from the peptide's pI, the higher the dried peptide's solubility when subsequently combined with other solvents, particularly organics and aqueous mixtures thereof, as well as the non-aqueous hydrophobic vehicle. Generally, the pH of the solution or suspension from which the peptide material is dried is greater than about 0.2, 0.3, 0.4, or 0.5 pH units from the pI of the peptide active agent, usually greater than about 0.6, 0.7, 0.8, or 0.9 pH units from the pI of the peptide active agent, and more usually about 1 pH unit or greater from the pI of the peptide active agent.

In one embodiment, the peptide active agent can be or lyophilized or dried in a stable form at a pH at which the peptide is highly charged, and in a further embodiment at a pH at which the peptide active agent is mostly charged thus owning the highest possible number of charges.

When the stably hydrated peptide active agent is prepared in this manner and formulated with the non-aqueous hydrophobic vehicle without further rounds of solvent exchange and/or drying, the benefit of complexation and the solution or suspension pH from which the peptide material was originally dried can effectively be maintained. However, such benefit can be lost or substantially reduced unless care is taken to maintain stable hydration of the peptide. Specifically, reliable and reproducible mucosal delivery of the peptide active agent is adversely affected if the peptide is not stably hydrated.

For example, when subjecting a stably hydrated peptide active agent to further processing steps involving solvent exchange and drying (e.g., desalting, counter ion exchange, and/or preparing the preformed peptide complex ex situ), stable hydration can be achieved and/or maintained by processing the stably dried peptide active agent in, and drying the resulting peptide material from a solution or suspension at a pH different, optionally remote, from the pI of the peptide active agent, as described above. In certain embodiments, the pH of the solution or suspension can be adjusted by the careful addition or acid and/or base to achieve a target pH, typically a target pH in the range of about 0.5 to 8.5, more often from 2.0 to about 8.0, usually about 4.0 to 8.0 (depending on the pI of the peptide active agent), with the optional inclusion of one or more additional pharmaceutically acceptable excipients, such as buffer, isotonic agent, preservative, antioxidant, and the like to aid in the maintenance of the stably hydrated peptide active agent. In a specific embodiment, the solution or suspension in which the pH is adjusted is water, and/or acetonitrile/water mixtures, particularly acetonitrile/water mixtures that contain about 10%-90% acetonitrile, including about 20%-80%, 30%-70%, 40%-60%, and more particularly about 55%-65%, usually about 50:50 mixtures.

Stable hydration can also be achieved and/or maintained by processing the stably hydrated peptide active agent, and drying the resulting peptide material from a solution or suspension comprising aqueous, organic, or mixtures thereof, provided drying is carried out under conditions that avoid unwanted water loss, particularly by maintaining appropriate temperature, pressure and drying time (e.g., about or less than 40° C., such as about or less than 35° C., typically about or less than 32° C., for about or less than 3 hours, such as less than 2 hours, more typically less than 1.5 hours, in a centrifugal evaporator/SpeedVac). Here again one or more additional pharmaceutically acceptable excipients can be added for stability.

The various processing steps discussed above may employ solutions or suspensions that are aqueous, organic, or mixtures thereof, usually depending on the particular processing step (e.g., water, acetonitrile, methanol, ethanol, aqueous mixtures thereof etc.), or organic solvents alone. In certain embodiments, particularly for peptide complex formation ex situ, the solution or suspension is an aqueous alcohol, such as an aqueous methanol or aqueous ethanol, including an aqueous alcohol having a water content of about 1% to 50% by volume, such as about 1% to about 25%, particularly about 1% to 15%, and more particularly about a 2 to 8% aqueous alcohol, such as an aqueous alcohol having a water content of about 5% by volume. Aqueous methanol solutions and suspensions are of specific interest, as methanol is the organic solvent closest to water and able to dissolve a very broad range of organic compounds. Additional mixtures are DMSO/Water and Acetonitrile/water.

Additionally, the various processing steps discussed above may be employed in any effective combination to produce the desired end composition, for example, in steps involving: (i) optional desalting of the peptide active agent; (ii) optional counter ion exchange of the peptide active agent; and/or (iii) peptide complex formation ex situ and formulation in the non-aqueous hydrophobic vehicle, and/or peptide complex formation in situ in the non-aqueous hydrophobic vehicle; with the proviso that the peptide active agent is processed under conditions that take into consideration the pI of the peptide active agent and retain a sufficient amount of water in association with the peptide to maintain solvation and stability of the peptide.

In addition to the pI and hydration of the peptide active agent in complex with a crown compound and/or counter ion, it has been found that mucosal delivery of the peptide active agent can be further improved by other aspects of the disclosure, including choice of the crown compound, counter ion, and amounts thereof, as well as choice of the non-aqueous hydrophobic vehicle, optional excipients and amounts thereof.

For example, the peptide active agent is complexed with a sufficient amount of a complexing agent, such as a crown and counter ion of interest, which can be present in molar excess of the peptide active agent, generally in a ratio of about 2 to 1, 5 to 1, 10 to 1, 15 to 1, 20 to 1, 30 to 1, 60 to 1 or greater. Typically, the crown and counter ion components are complexed at a molar ratio dependent on the type and number of ionizable groups present on the peptide active agent. In one embodiment, the peptide active agent comprises one or more cationic groups (e.g., primary amine, a secondary amine, a guanidinium group, and combinations thereof), the crown compound is a cation-binding crown compound (e.g., a crown ether type compound), and the counter ion is an anionic counter ion (e.g., an acidic counter ion). Of particular interest is where the cation-binding crown compound and the anionic counter ion are each individually present at about 0.5 to 10 stoichiometric equivalents per cationic group, more particularly about 2 to 4 stoichiometric equivalents, and most particularly about 1 to 2 stoichiometric equivalents, per cationic group. In a specific embodiment, the cation-binding crown compound is present at about 2 stoichiometric equivalents per primary amine, secondary amine, and/or guanidinium group, and the cationic counter ion is present at about 1 stoichiometric equivalents per primary amine, secondary amine, and/or guanidinium group of the peptide active agent.

In another embodiment, the cationic group is associated with one or more neutralized carboxylates, which cationic group can be derived from inorganic species including but not limited to $Na^+$, $K^+$, $Li^+$, $Mg^{++}$, $Ca^{++}$ and the like.

Another feature in addition to the pI, the peptide hydration, and the crown/counter ion amounts, is the formulation and use of a non-aqueous hydrophobic vehicle having a pH range that stabilizes the peptide complex. For example, the benefit of complexation and controlling of the pH of solutions or suspensions from which a peptide active agent is prepared in and dried from can be lost or substantially reduced in mucosal delivery compositions if the pH of the non-aqueous hydrophobic vehicle strays too far out of the margin for maintaining the desired solubility of the peptide complex in the vehicle. Typically, the pH of the non-aqueous hydrophobic vehicle has a range of about +/−1 to about +/−4 pH units, usually about +/−3 pH units, such as a pH range of about 3-6, about 4-7, about 5-8, and more about usually about +/−2 pH units, such as a pH range of about 3-5, about 4-6, about 5-7, or about 6-8, and the like. Of course the final pH range of the non-aqueous hydrophobic vehicle can be adjusted, including by the addition of acid, base, buffer and/or other excipients, as well as by the addition of the peptide salt and/or peptide complex itself depending on the components and amounts in association therewith.

Although the pH range of the non-aqueous hydrophobic vehicle may overlap with the pI of the peptide active agent, in general, the farther away the vehicle's midpoint pH is from the peptide's pI, the higher the peptide complex's solubility in the vehicle. Also, by forming the peptide complex either in situ or ex situ at a pH remote from the pI of the peptide active agent, the target pH is readily approached without unnecessarily having to cross over the pI of the peptide active agent upon combination of the material with the vehicle. For example, for a peptide active agent with a pI of about 5.0, and a non-aqueous hydrophobic vehicle having a pH range of about 3.0 to 6.0, the peptide salt or peptide complex can be prepared ex situ by drying the material from a solution or suspension at a pH greater than 5.0, usually at least 1 pH unit greater, again with the proviso that the peptide active agent is processed under conditions that retain a sufficient amount of water in association with the peptide to maintain solvation and stability of the peptide. After combination, if desired, the pH of the combined mixture can be further adjusted and/or allowed to equilibrate in the composition to achieve solvation.

These findings are significant as certain mucosal delivery compositions, such as those comprising a non-aqueous hydrophobic vehicle having at least one acylglycerol and at least one organic solvent and/or lipid, significantly enhance, and in many cases, make possible mucosal delivery of an effective amount of the peptide active agent, among other desirable aspects, including storage stability. For example, in certain embodiments the non-aqueous hydrophobic vehicle comprises at least one acylglycerol, and at least one organic solvent, and optionally at least one lipid, each individually present in an amount effective to (i) solubilize the stably hydrated peptide active agent complexed with the crown compound and the counter ion, and (ii) enhance mucosal delivery of the peptide active agent. In this regard, "non-aqueous" is intended to mean less than about 10% water, more particularly, less than about 5% water. Thus, the mucosal delivery composition generally includes various solubilizing agents in non-aqueous medium, such as a medium comprising an acylglycerol, and an organic solvent, and optionally a lipid such as a fatty acid or neutral lipid (as described in greater detail below). The mucosal delivery composition and components thereof may also include one or more additional pharmaceutically acceptable excipients (as described in greater detail below), such as one or more of a non-ionic surfactant, antioxidant, buffer, viscosity modifier, preservative, isotonic agent, chelating agent, and the like. As such, by employing such non-aqueous hydrophobic vehicles having a pH range that stabilizes the peptide complex, and/or one of more additional features as noted above, the benefits of the subject disclosure can be maximized.

As summarized above, an effective amount of the stably hydrated peptide active agent complex is solubilized in a mucosal delivery composition, and thus capable of delivering of an effective amount of the peptide active agent into the blood stream of the host when administered to a mucosal membrane thereof. In certain embodiments, mucosal delivery of the peptide active agent as provided in the mucosal delivery compositions of the disclosure is enhanced relative to the peptide active agent that is not stably hydrated. Of particular interest is where the enhancement is greater than about 10%, 20%, 30%, 40%, 50%, 60%, 70%, 80%, or 90%, and usually greater than about 100% (i.e., 1-fold or greater).

For example, the amount of the peptide active agent that enters the blood stream of a host can be measured qualitatively and/or quantitatively, directly and/or indirectly, by various techniques known in the art, such as by chromatography (e.g., HPLC, Mass-Spectrophotometry etc.), enzymatically (measuring substrate consumption and/or modification, or product and/or by-product production), antigen-antibody binding (e.g., Western Blot, Enzyme-Linked ImmunoSorbent Assay (ELISA) etc.), by biological effect (e.g., pharmacological bioavailability by indirect measure of amount of the peptide active agent that enters the blood stream, such as illustrated in the experimental section below), and the like. By comparing amounts of the peptide active agent that enter the blood stream of a host by one or more of such techniques, the enhancement can be readily determined.

As such, in certain embodiments, the mucosal delivery composition exhibits pharmacological bioavailability of the peptide active agent that is greater than about 10% relative to intrapleural (pI) administration, usually greater than about 15%, and typically about 16%, 17%, 18%, 19%, 20% or greater. In a specific embodiment, the peptide active agent upon sublingual administration of the mucosal delivery composition has a pharmacological bioavailability of greater than about 10% relative to intrapleural administration, usually greater than about 15%, and more typically about 20% or greater.

In certain embodiments, mucosal delivery of the peptide active agent as provided in the mucosal delivery compositions of the disclosure is enhanced and reliably reproducible relative to the peptide active agent that is not stably hydrated. By "reliably reproducible" is intended the extent to which the measurements of a test remain consistent over repeated tests of essentially the same composition under identical conditions. As such, mucosal delivery using a mucosal delivery composition of the disclosure is reliably reproducible if it yields consistent results of substantially the same measure. Conversely, mucosal delivery of a mucosal delivery composition is unreliable if repeated tests give inconsistent results of substantially different measure.

In further describing the subject disclosure, specific components or compositions are now reviewed separately in greater detail.

Stably Hydrated Peptide Active Agent

The stably hydrated peptide active agent has a water content by weight and solubility in an organic or aqueous organic solvent comparable to or greater than the dried peptide active agent, and is essentially non-aggregated and unoxidized.

In one embodiment, the stably hydrated peptide active agent has a water content by weight and solubility in an organic or aqueous organic solvent comparable to or greater than the peptide active agent dried (i) from a solution or suspension at a pH different, optionally remote, from the isoelectric point of the peptide, and (ii) under conditions that retain a sufficient amount of water to maintain solvation and stability of the peptide.

In a related embodiment, the stably hydrated peptide active agent has a water content by weight comparable to a storage stable dried form of the peptide. In this regard, storage stability of the dried form of the peptide is determinative when having a shelf life equal or greater than one month when stored at a temperature in the range of $-20°$ C. to $25°$ C. In many embodiments, the storage stable dried form of the peptide is associated with one or more pharmaceutically acceptable excipients, for example, co-drying excipients such as counter ion, preservative, isotonic agent, and/or buffer.

As such, the water content of the stably hydrated peptide active agent relative to the anhydrous peptide can be about 0.1% to about 50% by weight, and is usually about 0.5% to about 50%, 1% to about 30%, 1% to about 25%, more usually about 1% to about 20%, about 1% to about 15%, and typically about 1% to about 10%, such as about 1% to about 5%.

Peptide hydration can be measured relative to the anhydrous peptide by standard techniques known in the art. For example, water content can be measured using the Loss On Drying method and/or the Karl-Fischer method (e.g. J. A. Dean, Analytical Chemistry Handbook, Section 19, McGraw-Hill, New York, 1995, or by the United State Pharmacopeia's (USP) publication USP-NF (2004), which describes the US Food and Drug Administration (FDA) enforceable standards ((2004—USP—Chapter 921).

Regarding solubility, the stably hydrated peptide active agent has a percent solubility value in a given organic or aqueous organic solvent at ambient temperature that is equal to or greater than 0.001%, usually less than or equal to 125% of the percent solubility value, and typically less than or equal to the percent solubility value of the peptide active agent dried from a solution or suspension at a pH different, optionally remote, from the isoelectric point of the peptide. Solubility in organic or aqueous organic solution or suspension is readily measured as the concentration wherein adding more of the peptide does not increase its concentration in the solution or suspension. Solubility can also be estimated by visual inspection in relatively clear liquid or gel formulations (e.g., solubilized if peptide formulation is essentially limpid in appearance).

pH and pI

The pH of a subject composition is targeted so that the peptide active agent is sufficiently ionized to maintain complexation with the desired complexing agent(s), as well as capable of being soluble or re-soluble when combined in the non-aqueous hydrophobic vehicle. For example, complexation with a cation-binding crown compound is favored when amino groups of the peptide are protonated (ionized). Accordingly, the pH of the subject compositions is different, often remote, from the pI of the peptide active agent in the composition, where the peptide is sufficiently ionized for complexation with the crown compound and counter ion. By "isoelectric point" is intended the pH value at which the peptide active agent carries no overall net electrical charge.

In general, the pH is selected such that the peptide complex remains stable and soluble (or re-soluble when prepared as a dried, preformed peptide complex). By "remote from the isoelectric point of the peptide active agent" is intended about 1 pH unit or greater from the isoelectric point of the peptide active agent. The pH may be above or below the isoelectric point of the peptide active agent, provided it is within a range that stabilizes the stably hydrated peptide active agent in the composition for a given end use. Thus certain embodiments, the pH is above the pI of the peptide active agent, whereas in other embodiments, the pH is below the pI of the peptide active agent. In certain embodiments, the pH is about 0.1 to about 4 pH units from the isoelectric point of the peptide active agent. In some embodiments, the pH is about 0.5 to about 3 pH units, including about 1 to about 2 pH units, from the isoelectric point of the peptide active agent.

The actual pH of a given composition can be readily determined and adjusted to maintain stability of the stably hydrated peptide active agent complexed with the crown compound and/or counter ion alone, and/or in the non-aqueous hydrophobic vehicle. In certain embodiments, a buffer is included to maintain the pH within a given range. The pKa of buffer in solvent mixtures containing predominantly water, are close to the water value. In contrast, as the proportion of organic solvent increases, the buffer pKa changes. For example, neutral weak acids such as acetic acid and anionic acids such as $H_2PO_4^-$ typically get weaker, and the pKa becomes larger as the proportion of organic solvent increases. Cationic acids such as $NH_4^+$ get stronger, but this trend reverses at high organic concentration and they become weaker.

Accordingly, the pH can be approached empirically, and/or estimated by calculation of the solution pH with reference to standard buffer solutions of known pH (e.g., Rondinini, S., *Analytical Bioanalytical Chem* (2004) 374(5):813-816; Bosch et al., *Anal. Chem.* (1996) 68(20):3651-3657; Subirats et al., *J Chrom A*, (2007) 1138:203-215; Subirats et al. *Separation & Purification Reviews* (2007) 36(3):231-255; and Gagliardi et al. *J. Chromatography A* (2005) 1077(2): 159-169). The pKa (and isoelectric point) values of peptides under such conditions can also be determined (e.g., Sanz-Nebot et al., *J. Chromatography A* (2002) 942(1-2):145).

When including a counter ion and/or buffer, considerations for selection include buffering capacity, solubility, and ionic strength in the composition. Thus, optimizing the pH to increase the ratio of the ionized to the neutral form of the peptide (i.e., away from the isoelectric point of the peptide) can be accomplished in aqueous, organic, and aqueous organic solutions to favor crown and counter ion complexation.

Peptide Active Agent

Peptide active agents of the present disclosure are those peptides whose mucosal delivery is facilitated or enhanced when administered in conjunction with the subject mucosal delivery compositions and methods. Whether or not a given peptide active agent is suitable for use according to the present disclosure can be readily determined, for example, using assays employed in the experimental section below. Generally, a peptide active agent is suitable for use in the subject methods if its mucosal delivery in conjunction with the subject non-aqueous hydrophobic vehicle of the disclosure delivers an effective amount of the agent into the blood stream of the host, particularly where such delivery is increased by 1 to 10-fold or more, such as by 50-fold or more and sometimes by 100-fold or more relative to mucosal administration of the peptide in the absence of the mucosal delivery vehicle (e.g., peptide in sterile saline solution), as determined by measuring peptide concentration present in the blood stream of a host, for example, using detection systems suitable for such purposes as discussed above and illustrated in the experimental section below. In certain embodiments, the peptide active agent is one whose occurrence and/or intensity of observable biological effects are increased by mucosal delivery, for example, as observed in the mouse assay described in the experimental section below.

Examples of peptides of interest include, but are not limited to, acetalins (e.g., acetalin 1, 2 and 3 (acetyl plus enkephalin), adrenocorticotropic hormone (ACTH) and related peptides, adipokinetic hormones (e.g., adrenomedullin), ADP-ribosylation factors (ARF), adrenomedullin peptides, Agouti related peptides, allatostatins, amylin peptides, amyloid peptides, angiotensins and related peptides, annexin, various anti-inflammatory peptides, antimicrobial and related peptides, antioxidant peptides, apelin peptides, apoptosis peptides, Bad and Bag Cell peptides, adrenal medulla peptides, basic fibroblast growth factor (bFGF), bombesins, bradykinins, C-Peptides, C3a peptides, calcitonin and related peptides, CART (cocaine- and amphetamine-regulated transcript) peptides, casomorphins, caspase related peptides, cell adhesion peptides, cholecystokinin-pancreozymin peptides, corticotropin related peptides, cytochromes and related peptides, cytokines (e.g., granulocyte-colony stimulating factor, erythropoietin, etc.), chemokines, defensins, dynorphins, endomorphins, endorphins, endothelins, enkephalins, exendins, fibrinogen and related peptides, fibronectin fragments, galanins, gastric inhibitory peptides (GIPs), gastrins, ghrelins, glucagon, glucagon-like peptides, growth factors, growth hormone related peptides, guanylins, heat shock proteins, hepatitis C virus (HCV) related peptides, high mobility group (HMG) peptide, HIV related peptides, integrins, interleukins, interferons, kinases/phosphatase substrates, luteinizing hormone-releasing hormones and related peptides, matrix metalloproteinases (MMPs), melan-A and mucin related peptides, melanocyte stimulating hormones and analogs, myelin basic proteins (MBPs), myosin, natriuretic peptides, neurokinins, neuromedins, neuropeptide Y and analogs, neuropeptides, neurotensins and related peptides, NF-kB/transcription factors related peptides, orexins, osteocalcin fragments, OVA peptides, oxytocins, vasopressins, desmopressin and related peptides, pancreatic polypeptides, parathyroid hormones and related peptides, peptide YY and analogs, peptidoglycan peptides, phosphopeptides, phytochelatins, pituitary adenylate cyclase activating peptides (PACAPS), prion protein (PrP) fragments, prolactin releasing peptides, proteolipid proteins (PLPs), salusin peptides, saposin related peptides, secretins, selectin related peptides, signal transduction peptides, somatostatins, substance P and analogs, tachykinin related peptide, thrombin related peptides, thrombospondins, thyrotropin releasing hormones and related peptides, TNF peptides, toxins, urotensin related peptides, vasoactive intestinal peptides (VIPs), vasopressin related peptides, viral peptides, and the like.

Of particular interest are peptide hormones, which are a class of peptides that exhibit activity upon entry into the blood stream and have endocrine functions in living animals. Examples of peptide hormones of specific interest include, but are not limited to, glucagon, glucagon-like-peptide, insulin, somatostatin, calcitonin, parathyroid hormone, and the like, and analogues/derivatives thereof. Thus in certain embodiments, the peptide active agent is a peptide hormone, for example, insulin and the incretin mimetics, such as the exendins and related analogues/derivatives (e.g., chemically synthesized and/or biologically produced exendins such as exendin-3 and exendin-4, liraglutide, glucagon-like peptide-1 (GLP-1), and Taspoglutide, Albiglutide, ZP10 (AVE0010), and various analogues/derivatives thereof.

Naturally occurring incretins such as GLP-1 exhibit insulinotropic properties after release into the circulation from the gut. The actions of GLP-1 include (a) a stimulation of insulin secretion in a glucose-dependent manner, (b) a suppression of glucagon, (c) a reduction in appetite and food intake, (d) a deceleration of gastric emptying, (e) a stimulation of β-cell neogenesis, growth and differentiation in animal and tissue culture experiments, and (f) an in vitro inhibition of β-cell apoptosis induced by different toxins.

Naturally occurring exendins are peptide hormones isolatable from an exocrine gland but have endocrine actions. Exendins stimulate insulin secretion in response to rising blood glucose levels, and modulate gastric emptying to slow the entry of ingested sugars into the bloodstream. Exendin-3 is a 39-amino acid peptide that shares homology with VIP (vasoactive intestinal peptide), secretin, helospectin I and II and helodermin. It stimulates increases in cellular cAMP and amylase release from dispersed guinea pig pancreatic acini. Exendin-4, a 39-amino acid peptide originally isolated from the oral secretions of the lizard *Heloderma suspectum*, has been shown to share certain activities with glucagon-like-peptide-1 (GLP-1).

Exenatide (the active ingredient of BYETTA® (exenatide injection), also called exendin-4) is a GLP-1 agonist that improves glucose homeostasis by mimicking the actions of naturally occurring GLP-1. It improves glycemic control by reducing fasting and postprandial glucose concentrations through a combination of known mechanisms, including glucose-dependent insulin secretion, restoration of first-phase insulin response, regulation of glucagon secretion, delaying gastric emptying, and decreasing food intake.

As a drug, Exenatide is a subcutaneously injected incretin mimetic peptide approved for the treatment of type 2 diabetes mellitus (condition in which the body does not use insulin normally and, therefore, cannot control the amount of sugar in the blood). Exenatide is used in combination with metformin, a sulfonylurea, or a thiazolidinedione. Exenatide works by stimulating the pancreas to secrete insulin when blood sugar levels are high. Insulin helps move sugar from the blood into other body tissues where it is used for energy. Exenatide also slows the emptying of the stomach and causes a decrease in appetite. Exenatide is not used to treat type 1 diabetes (condition in which the body does not produce insulin and, therefore, cannot control the amount of sugar in the blood). Exenatide is usually injected twice a day within 60 minutes before the morning and evening meals.

Liraglutide is a GLP-1 derivative that finds use similar to Exenatide, for example, in the treatment of type 2 diabetes. Liraglutide has a half-life after subcutaneous injection of 11-15 hours, making it suitable for once-daily dosing (in contrast to Byetta's twice daily). The prolonged action of liraglutide is achieved by a fatty acid molecule attached to the GLP-1 molecule, which binds to albumin within the subcutaneous tissue and bloodstream. The active GLP-1 is then released from albumin at a slow, consistent rate. Binding with albumin also results in slower degradation and reduced elimination of liraglutide from the circulation by the kidneys compared to GLP-1.

Thus, peptide active agents for use in the subject methods and compositions of the disclosure may include incretin mimetics, such as GLP-1, and various analogues/derivatives thereof including exendin-4, liraglutide, and various analogues/derivatives thereof. Incretin mimetics and related compounds of interest are described in U.S. Pat. Nos. 5,118,666; 5,120,712; 5,187,154; 5,264,372; 5,376,637; 5,424,286; 5,512,549; 5,545,618; 5,552,520; 5,574,008; 5,614,492; 5,631,224; 5,686,511; 5,846,937; 5,958,909; 6,162,907; 6,191,102; 6,268,343; 6,284,727; 6,358,924; 6,448,045; 6,458,924; 6,506,724; 6,528,486; 6,703,359; 6,706,689; 6,723,530; 6,767,887; 6,828,303; 6,849,708; 6,852,690; 6,858,576; 6,872,700; 6,884,585; 6,899,883; 6,902,744; 6,911,324; 6,924,264; 6,956,026; 6,982,248; 6,989,148; 6,989,366; 7,022,674; 7,056,734; 7,056,887; 7,078,375; 7,084,243; 7,115,569; 7,119,168; 7,138,375; 7,138,486; 7,153,825; 7,157,555; 7,164,005; 7,220,721; 7,223,725; 7,226,990; 7,259,234; 7,273,850; 7,297,761; 7,307,148; the disclosures of which are herein incorporated by reference.

Additional peptide active agents for use in the subject methods and compositions of the disclosure may include insulin, such as human insulin and various analogues/derivatives thereof. Insulin and related compounds of interest are described in U.S. Pat. Nos. 4,511,505; 5,631,347; 5,646, 242; 5,693,609; 5,700,904; 5,750,497; 5,922,675; 6,011, 007; 6,051,551; 6,159,931; 6,162,895; 6,268,335; 6,309, 633; 6,444,641; 6,465,426; 6,531,448; 6,713,452; 6,770, 625; 6,828,297; 6,835,802; 6,858,580; 6,867,183; 6,869, 930; 6,913,903; 7,030,084; 7,060,675; 7,084,114; 7,084, 121; 7,166,571; 7,169,889; 7,196,059; 7,211,557; 7,273, 921; 7,312,192; the disclosures of which are herein incorporated by reference.

Further peptide active agents for use in the subject methods and compositions of the disclosure may include parathyroid hormone, or calcitonin (e.g., for the treatment of Paget's disease, hypercalcemia and osteoporosis, including natural, synthetic or recombinant human, salmon, pig or eel calcitonin). Parathyroid hormone, calcitonin and related compounds of interest are described in U.S. Pat. Nos. 4,692,433; and RE40,850; the disclosures of which are herein incorporated by reference.

In certain aspects of the subject methods and compositions, the peptide active agent is incretin mimetic peptide. In a featured embodiment, the incretin mimetic is exendin-4 and analogues/derivatives thereof. In a featured embodiment, the incretin mimetic is liraglutide and analogues/derivatives thereof. In other embodiments, the peptide active agent is glucagon-like peptide-1 (GLP-1) and analogues/derivatives thereof. In yet other embodiments, the peptide active agent is insulin and analogues/derivatives thereof. In some embodiments, the peptide active agent is other than a peptide selected from one or more of the peptides described herein, such as insulin, including peptides larger than about 50 amino acids, such as peptides larger than about 100 amino acids.

The scope of the present disclosure also includes prodrugs of the peptide active agents. Such prodrugs are, in general, functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include peptides bearing post-translational or synthesis modification sites, enzymatic or chemically cleavable bonds, such as peptides with protease cleavable leader residues or sequences, or esters that hydrolyze in vivo (e.g., in the human body) to produce a compound described herein suitable for the present disclosure. Suitable ester groups include, without limitation, those derived from pharmaceutically acceptable, aliphatic carboxylic acids, particularly alkanoic, alkenoic, cycloalkanoic and alkanedioic acids. Illustrative esters include formates, acetates, propionates, butyrates, acrylates, citrates, succinates, and ethylsuccinates.

Crown Compound

The crown compounds include, for example, cyclic polyethers (crown ethers, e.g., 18-crown-6) and cyclic polyesters (crown esters, e.g., polylactones such as nonactine and tetranactine, polyglycolic or lactic esters), and analogues/derivatives thereof (e.g., WO 08/037,484; Lifson et al., J. Am. Chem. Soc. (1983) 105:3866-3875; Lifson et al., J. Am. Chem. Soc. (1984) 23:2577-2590; and McGeary et al., Tetrahedron (2000) 56:8703-8713; which references are incorporated herein in their entirety). Of particular interest are crown compounds selected from (i) cyclic polyester; (ii) cyclic polyamide; (iii) cyclic polyether; (iv) cyclic polyoxime; (v) polythioester; (vi) polymer of aminoxy acids; (vii) polydisulfide; (viii) cyclic polydioxanones, and (ix) a cyclic compound belonging to more than one of (i) to (ix), where the crown is a cation-binding crown compound capable of forming a charge masking complex with a cation, such as protonated primary amino groups (—NH$_3^+$), and/or protonated secondary amino groups (—NH$_2^+$—), and/or a protonated guanidinium groups (—NH—C($=$NH$_2^+$)—NH$_2$).

In certain embodiments, the crown compounds are cyclic polyethers, cyclic polyesters, and cyclic depsipeptide (where "depsipeptide" refers to crown compounds which comprise or consist of alpha-hydroxy acids and alpha-amino acids, or mixtures thereof, which are linked to each other by ester linkages between the hydroxy group of an alpha-hydroxy acid and the carboxyl group of either a hydroxy acid or an amino acid as well as by amide linkages between the amino group of an alpha-amino acid and the carboxyl group of either a hydroxy acid or an amino acid). Linear forms of the subject crown compounds, such as a cleavage form thereof, may be employed as charge complexing agents in some aspects of the disclosure.

As such, the crown compound in certain embodiments comprises a biodegradable linkage. In general, the biodegradable linkage is cleavable in vivo. Examples of biodegradable linkages of particular interest include esters, such as carboxylic acid esters (—C(O)—O—), thioesters (—C(O)—S—), orthoesters (—C(OR$^1$)(OR$^2$) and (—C(OR$^1$)(OR$^2$)(OR$^3$)), and the like. Additional examples of biodegradable linkages include disulfides (—S—S—), Schiff base (R$^1$R$^2$C$=$N—R$^3$), and the like. Of particular interest is where the biodegradable linkage is an ester, and more particularly an ester selected from a carboxylic acid ester, and an orthoester. Crown compounds of specific interest are disclosed in the co-pending patent application entitled "Orthoester derivatives of crown ethers" and having Application No. 13/511,837, filed on Aug. 16, 2012, which reference is incorporated in its entirety. Examples of carboxylic acid ester and an orthoester crown compounds include, but are not limited to, the oxo-crowns and analogues/derivatives thereof, particularly oxo-crown ethers.

In one embodiment, the oxo-crown ethers comprise 4 to 8 coordinating oxygen ring atoms, 8 to 16 ring carbon atoms, and at least one oxo-substituted side chain. Of specific interest are oxo-(18-crown-6) compounds and analogues/derivatives thereof, such as those comprising a structure selected from oxo-(18-crown-6), oxo-(18-crown-6)-diethyl tartrate, and oxo-(18-crown-6)-diglycerol tartrate, as illustrated below.

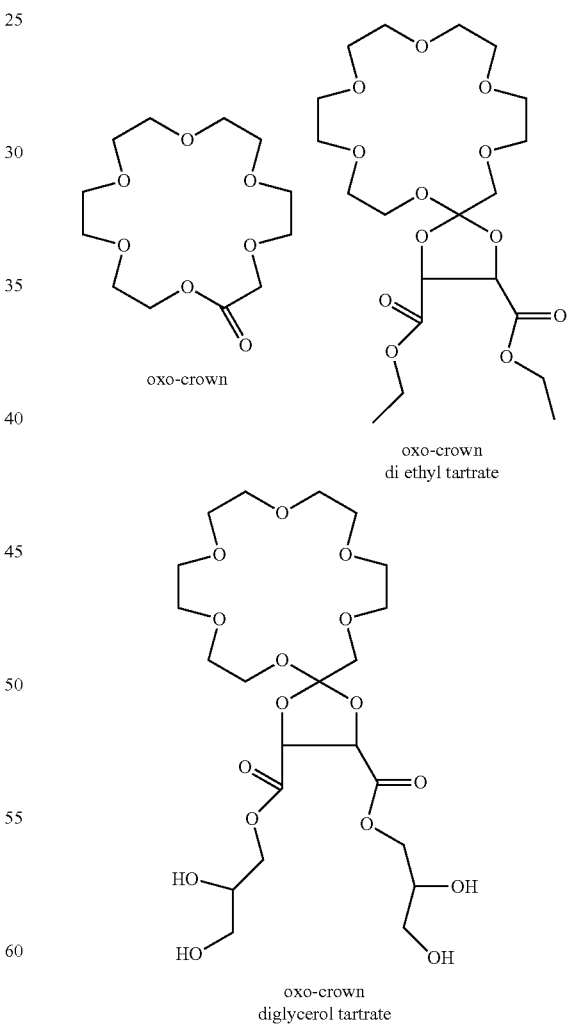

oxo-crown oxo-crown di ethyl tartrate oxo-crown diglycerol tartrate

Counter Ion

The presence of the counter ion allows the formation of neutrally charged species of ionizable groups of the stably hydrated peptide active agent. In general, the counter ion is present in an amount in combination with the crown compound under conditions that partially neutralize, or impart overall neutrality to the stably hydrated peptide active agent. In certain embodiments, the counter ion is a counter ion of an acidic salt (e.g., salicylic acid, acetic acid, trifluoroacetic acid, tartaric acid, phosphoric acid, lactic acid, fumaric acid, maleic acid, citric acid, methylsulfonic acid, p-toluenesulfonic acid), an amino acid (e.g., lysine, glycine, histidine, arginine), or a modified amino acid (e.g., N-acetyl-lysine-amide, N-acetyl-arginine-amide). Combinations of different counter ions are also contemplated.

Thus, in some embodiments, the counter ion is selected from an acidic salt, an amino acid, a modified amino acid, and mixtures thereof. One aspect is where the counter ion of an acidic salt is a hydrophilic acid or lipophilic acid. Examples of hydrophilic acids of interest include, but are not limited to, trifluoroacetic acid, sulfonic acid, and benzoic acid. Examples of lipophilic acids of particular interest included, but are not limited to, aryl and alkyl sulfonic acids, such as dodecyl-sulfonic acid and higher homologues, phosphatidylglycerol derivatives such as dilauryloylphosphatidylglycerol (DLPG), lipoic acid, and the like. As such, other suitable lipophilic acids can be employed. Of specific interest is a counter ion of an acidic salt that is a strong lipophilic acid, such as an alkyl sulfonic acid and higher homologues. In certain embodiments, the hydrophilic acid is selected from the group consisting of trifluoroacetic acid, sulfonic acid, and benzoic acid. In other embodiments, the lipophilic acid is dodecyl-sulfonic acid. When employing relatively strong acidic counter ions, such as dodecyl-sulfonic acid, care is taken to avoid oxidation of peptides that may be susceptible, for example, by inclusion of an antioxidant, limiting the concentration of the counter ion, and so forth.

As noted above, lipophilic acids, such as alkyl sulfonic acids having an alkyl chain with between 2 and 30, and usually between 8 and 10 carbon atoms are of specific interest. Aryl sulfonic acids with one or more alkyl substituents on the aromatic ring, each alkyl substituent generally having between 2 and 30, more generally between 8 and 10 carbon atoms, are further examples of suitable counter ions. Certain phospholipids may also be employed as a counter ion in some embodiments. For example, phospholipids with at least an acidic proton on the phosphate, such as a phosphatidyl glycerol or phosphatidyl sugar with one acidic proton, or a phosphatidic acid with two acidic protons are of interest. The alkanoic acids comprised in such phospholipids or the phosphatidyl moieties, respectively, generally have between 4 and 30 each, more typically between 6 and 20, and usually between 8 and 18 carbon atoms. Phospholipids comprising two alkanoic acids may either symmetric or asymmetric. In the latter case, a phospholipid molecule comprises two different fatty acids. In another embodiment, the phospholipids are of natural origin, like for example phosphatidylinositol.

In certain embodiments of interest the counter ion can be acids with multiple acidic valence (multi protic) or poly carboxylic acids. Of particular interest are inorganic acids that include, but are not limited to, phosphoric sulfuric acid, and the like, and organic acids that include, but not limited to, bis-carboxylic aromatic acids such as Phthalic acid and Terephthalic Acid, and from alkylic oxalic acid, malonic acid, succinic acid, tartaric acid, maleic acid, fumaric acid, and the like.

Indeed, in a particular embodiment, a bis carboxylic acid of choice can be used as a counter ion to generate a cationic charge with an amino group of the peptide side chain, notably Lysine and Arginine. Thus in a specific embodiment, a peptide active agent can be prepared having about 1 bis carboxylic acid as per amino group counter ion, and then the pH can be brought to about neutrality, from approximately pH 6 to pH 8. Under such conditions the amino groups on the peptide chain (especially Lysine and Arginine) can still be fully protonated by the first acidic moiety of the acid, and the other acid function being concomitantly ionized and amenable of forming a salt with the buffer generating an additional cationic charge, for example sodium or potassium. Under this strategy, the cationic charges of peptide can be significantly increased possibly resulting in better solubility, reduced aggregation and enhanced peptide stability.

Non-Aqueous Hydrophobic Vehicle

The non-aqueous hydrophobic vehicle is generally capable of solubilizing, or maintaining the solubility of the peptide complex and/or peptide salt homogeneously dispersed therein. Thus the peptide complex and/or peptide salt when combined in the non-aqueous hydrophobic vehicle may be clear or turbid in appearance, with the proviso that an effective amount of the peptide active agent is homogenously dispersed therein without unwanted precipitation and/or aggregate formation. As described above, of particular interest is where the non-aqueous hydrophobic vehicle of the mucosal compositions comprises at least one acylglycerol, and at least one organic solvent and/or lipid each individually present in an amount effective to (i) solubilize the stably hydrated peptide active agent complexed with the crown compound and/or the counter ion and (ii) enhance mucosal delivery of the peptide active agent.

Acylglycerol

The acylglycerol embodies the water insoluble esters of glycerol (propane-1,2,3-triol) with fatty acids, and can be subdivided into mono-, di- or tri-O-acylglycerol (i.e., 1- or 2-monoglycerides; 1,2- or 1,3-diglycerides; and triglycerides, according to the number and position of acyl groups, as well as mono-di-glycerides and so forth for mixtures). Examples of the acylglycerol include, but are not limited to, corn oil mono-di-tridiglycerides, medium chain ($C_8$-$C_{10}$) mono- and diglycerides, long-chain triglycerides (castor oil, corn oil, cottonseed oil, olive oil, peanut oil, peppermint oil, safflower oil, sesame oil, soybean oil, hydrogenated soybean oil, hydrogenated vegetable oils), and medium-chain triglycerides (such as caprylic/capric triglycerides derived from coconut oil or palm seed oil). Such acylglycerols are generally recognized as safe for use as direct food additives, as well as for cosmetic and pharmaceutical applications. Acylglycerols having substituted or unsubstituted, saturated or unsaturated aliphatic chains of about 8-10 carbons ($C_8$-$C_{10}$) and higher homologues are sparingly soluble or non-soluble in water, are of particular interest.

In certain embodiments, the acylglycerol is selected from monoacylgycerol, diacylglycerol, and mixtures thereof. Of particular interest are monoacylglycerols and diacylglycerols that are solid or semi-solids at ambient, normal room temperature, particularly medium chain ($C_8$-$C_{10}$) mono- and diacylglycerols. Thus, a featured aspect is directed to the medium chain ($C_8$-$C_{10}$) monoacylglycerols, such as mono-decanoyl-glycerol.

Depending on a given route of administration and dosage form, at least one acylglycerol may be included in an amount so that the formulation is liquid, gel, or a solid or semi-solid at a desired temperature. A solid oral delivery formulation, for example, may employ one or more particular acylglycerols in an amount such that the formulation is a solid or semi-solid at temperature of up to about 50° C. to about 55° C. Conversely, an acylglycerol formulation can be selected that is a liquid or gel at lower temperatures than this. For instance, an acylglycerol formulation can be selected such that at least one acylglycerol is included in an amount to provide a formulation that is solid at 4° C., and melts at room temperature, or at or around the temperature of the host, e.g., solid at 4° C. and is melted or begins melting around 37° C.-45° C. Of specific interest is an acylglycerol formulation that is a solid or semi-solid at temperatures less than about the body temperature of the host, such as an acylglycerol formulation that is a solid or semi-solid at less than about 37° C.-45° C. In general, an acylglycerol with such features (in addition to other components of a given formulation) can be chosen based on its melting temperature. Of particular interest are acylglycerols that are solids or semi-solids at ambient room temperature and having a melting temperature of about 60° C. or less, usually about 55° C. or less, and more typically about 53° C. or less, e.g., mono-decanoyl-glycerol, has a melting point of about 53° C. Many such acylglycerols are known and commercially available.

Of particular interest are the acylglycerols with unsaturated long alkyl chain (preferably C18-C21), such as mono-olein (glycerol ester with oleic acid), mono linolein, mono elaidin, mono eructate et others, which are liquids and or semi-solid at room temperature.

For example, medium chain ($C_8$-$C_{10}$) mono- and diacyl-glycerols typically are solids or semi-solids at temperatures less than about the body temperature of the host, and thus have, or can be formulated to have, melting points that are less than about the body temperature of the host, usually less than about 37° C., and as such are of specific interest. Thus, once such acylglycerol compounds are delivered to the host, the body temperature of the host can melt the semi-solid material, allowing for dissolution and delivery of the peptide active agent as desired.

Accordingly, acylglycerols that are a semi-solid at temperatures less than about the body temperature of the host can be advantageously used to (1) reduce the volume of the mucosal delivery vehicle, since solids or semi-solids have a reduced volume compared to their liquid forms, and (2) provide flexibility for solid or semi-solid dosage forms (as described in greater detail below). This aspect of the disclosure also aids in retaining the peptide active agent in the mucosal delivery composition to avoid unwanted leakage prior to delivery, more uniform dissolution of the peptide active agent upon delivery, enhancement of permeability in general across the mucosal membrane of interest, as well as maintaining the peptide active agent in its stably hydrated form in the mucosal delivery composition.

Thus is certain embodiments, the acylglycerol is a semi-solid at temperatures less than about the body temperature of the host. In a specific embodiment, the acylglycerol is a semi-solid at ambient, normal room temperature, such as a medium chain mono- and diacylglycerols. A featured aspect of the disclosure is directed to the medium chain ($C_8$-$C_{10}$) monoacylglycerols, such as mono-decanoyl-glycerol.

In other embodiments a mixture of one or more saturated acylglycerols (preferably C6-C24) can be used with one or more long alkyl chain unsaturated acylglycerol as defined above. Using such mixtures permits to optimize physical/chemical properties such as, but not limited to viscosity, and melting point of the composition of the invention.

Lipid

Lipids are generally defined as hydrophobic or amphiphilic small molecules. Examples of lipids include fats, waxes, sterols, fat-soluble vitamins (such as vitamins A, D, E and K), monoglycerides, diglycerides, phospholipids, and others. Thus in certain embodiments, the lipid component comprises an acylglycerol, for example, when the lipid is an oil, such as corn oil mono-di-tridiglyceride, long-chain triglyceride such as olive oil, castor oil, corn oil, cottonseed oil, peanut oil, peppermint oil, safflower oil, sesame oil, soybean oil, hydrogenated soybean oil, hydrogenated vegetable oils, medium-chain triglyceride such as caprylic/capric triglycerides derived from coconut oil or palm seed oil, and the like. In certain embodiments, the lipid is other than an acylglycerol, such as when the lipid is a fatty acid, or a neutral lipid such as a vitamin E (e.g., α-, β-, γ-, and δ-tocopherols and the corresponding four tocotrienols, which are fat-soluble neutral vitamins).

Of particular interest is where the lipid includes a fatty acid, more particularly, a permeability-enhancing fatty acid that is an aliphatic carboxylic acid, which may be saturated or unsaturated, branched or linear, and may include mixtures of different fatty acids. In addition to saturation, fatty acids are short, medium or long. Short chain fatty acids are fatty acids with aliphatic tails of less than seven carbons. Medium chain fatty acids are fatty acids with aliphatic tails of 7-14 carbons. Long chain fatty acids are fatty acids with aliphatic tails 16 carbons or more. Examples of fatty acids of particular interest include saturated fatty acids having 7-19 carbon atoms selected from caprylic acid, octanoic acid, nonanoic acid, decanoic acid, undecanoic acid, dodecanoic acid, myristic acid, palmitic acid, stearic acid, arachidic acid, and mixtures thereof. Examples of unsaturated fatty acids include those having 7-19 carbon atoms selected from palmitoleic acid, oleic acid, linoleic acid, alpha-linoleic acid, and mixtures thereof. Each of these fatty acids have found use in various consumables, including their use as food additives, in cosmetics, and pharmaceutical applications, and thus may be generally regarded as safe for their intended use.

One aspect of interest is the use of a permeability-enhancing fatty acid as an excipient of the mucosal delivery composition to aid and/or maintain the peptide active agent in its stably hydrated state. Permeability-enhancing fatty acids having from 7-14 carbon atoms, and particularly 7-12 carbon atoms for this purpose are of particular interest. A featured aspect is a permeability-enhancing fatty acid that is a saturated fatty acid selected from caprylic acid, octanoic acid, nonanoic acid, decanoic acid, undecanoic acid, dodecanoic acid. Of specific interest is nonanoic acid, and thus the fatty acids exhibiting its mucosal delivery properties when employed in the mucosal delivery composition of the present disclosure. The permeability-enhancing features of the fatty acid can be readily determined, such as illustrated herein.

In many embodiments, the non-aqueous hydrophobic vehicle comprises a non-aqueous solvent capable of solubilizing the stably hydrated peptide active agent complexed with the crown compound and/or the counter ion. The non-aqueous solvent according to the disclosure includes solvents which may be used as a constituent in a pharmaceutical or diagnostic composition and/or solvents which may be used during the course of the manufacture and formulation thereof. In other words, the medical use of such solvents is approved and/or their use does not pose a threat to the health of an individual to be treated. As such, the term "non-aqueous solvent" also includes natural products such as oils, and natural product derivatives such as Cremofor EL and the like.

Organic Solvent

In one embodiment, the non-aqueous hydrophobic vehicle comprises at least one organic solvent. The term "organic solvent" is known in the art and relates to carbon-based substances commonly used in the chemical industry, capable of dissolving or dispersing one or more substances. Generally speaking, organic solvents are more lipophilic or hydrophobic than water. As a consequence, their log P values are generally greater than zero.

Of particular interest are apolar organic solvents, organic solvents with a smaller dipole moment than water, as well as organic solvents which are hydrophobic, i.e. solvents which are hardly or not at all miscible with water. Organic solvents according to the disclosure refer to unsubstituted hydrocarbon solvents like paraffinic, aliphatic and aromatic hydrocarbons and their derivatives containing heteroatoms, like oxygen (e.g., alcohols, ketones, glycol esters), halogens (e.g., carbon tetrachloride), nitrogen (e.g., DMF, dimethyl formamide and acetonitrile) or sulphur (e.g., DMSO: dimethyl sulfoxide).

Commonly used organic solvents are methanol, ethanol, alcohols from $C_3$ to $C_{10}$, acetonitrile, butanone, 1,1,1-trifluoroethanol (TFE), hexafluoroisopropanol (HFIP), ethyl acetate, carbon tetrachloride, butanol, dibutyl ether, diethyl ether, cyclohexane, methylene chloride (dichloromethane), hexane, butyl acetate, di-isopropyl ether, benzene, dipentyl ether, chloroform, heptane, tetrachloroethylene, toluene, hexadecane, dimethylformamide (DMF), tetrahydrofurane (THF) and dioxane.

In certain embodiments, at least one organic solvent is a water soluble organic solvent. Examples of the water-soluble organic solvent include, but are not limited to, hexaethylene glycol, polyethylene glycol 300, polyethylene glycol 400, ethanol, propylene glycol, glycerin, N-methyl-2-pyrrolidone, dimethylacetamide, and dimethylsulfoxide. Each of these components is commercially available, found in a number of pharmaceutical products, and generally regarded as safe for their intended uses. Thus, in certain embodiments, the water-soluble organic solvent includes or consists of a humectant, such as a diol, polyol, or mixtures thereof. In other embodiments, the water-soluble organic solvent is a polar aprotic solvent. In some embodiments, the water-soluble organic solvent comprises a mixture of polar aprotic solvent with humectant.

A humectant is a hygroscopic substance having an affinity to form hydrogen bonds with molecules of water. It is typically a molecule with several hydrophilic groups, most often hydroxyl groups, but amines and carboxyl groups, sometimes esterified, can be encountered as well. Examples of humectants include glycerine, propylene glycol and glyceryl triacetate. Others can be polyols like the sugar alcohols erythritol, arabitol, xylitol, ribitol, mannitol, sorbitol, isomalt, maltitol, and lactitol, or polymeric polyols like polydextrose or natural extracts like quillaia, or polyethylene glycols like hexaethylene glycol (MW 282.3), polyethylene glycol 300 or polyethylene glycol 400.

In certain embodiments, one or more diols, polyols and mixtures thereof are included in the non-aqueous hydrophobic vehicle not only to aid solubilization of the stably hydrated peptide active agent, but also as a source of OH (hydroxyl) groups, which are amenable to hydrogen bonding with the peptide to aid in stabilization. As an example, peptides when formulated as dried powder or residue, particularly large peptides (e.g., proteins), may be dried with sugar alcohols such as mannitol to maintain folding and biological activity. This is because when formulated without water (in solution) and as dried powder or residue, it has been found that the peptides often loose biologically activity.

Of specific interest is a water-soluble organic solvent comprising a mixture of two or more of a polar aprotic solvent, propylene glycol, glycerol, and a polyethylene glycol. Glycerol (or propane-1,2,3-triol) is a colorless, odorless, viscous liquid is widely used in food and pharmaceutical formulations. Also commonly called glycerin or glycerine, it is a sugar alcohol, and is sweet-tasting and of low toxicity. Glycerol has three hydrophilic alcoholic hydroxyl groups that are responsible for its solubility in water and its hygroscopic nature. Propylene glycol (or propane-1,2-diol) is a diol alcohol, usually a tasteless, odorless, and colorless clear oily liquid that is hygroscopic and miscible with water, acetone, and chloroform. Because of its low chronic oral toxicity, propylene glycol is generally recognized as safe (GRAS) for use as a direct food additive, as well as for cosmetic and pharmaceutical applications. Polyethylene glycol (or PEG), also known as polyethylene oxide (PEO) or polyoxyethylene (POE), are polyethers. Of particular interest are PEG oligomers and polymers with a molecular mass below 20,000 g/mol, as well as various derivatives, the most common of which is a monofunctional methyl ether PEG (methoxypoly(ethylene glycol)), abbreviated mPEG. Of specific interest are PEG diols having a molecular mass below 8000 g/mol, 4000 g/mol, 1000 g/mol, 800 g/mol, 700 g/mol, or 600 g/mol, and particular PEG diols having a molecular mass of between about 200-500 g/mol, such as hexaethylene glycol, and the better known PEG 300 and PEG 400. As with the other components noted above, the subject PEG compounds are generally recognized as safe for use as a direct food additive, as well as for cosmetic and pharmaceutical applications.

Polar aprotic solvents are solvents that share ion dissolving power with protic solvents but lack an acidic hydrogen. These solvents generally have high dielectric constants and high polarity. Examples are N-methylpyrrolidone (or N-methyl-2-pyrrolidone), dimethyl sulfoxide, dimethylformamide, dioxane and hexamethylphosphortriamide. An advantage of polar aprotic solvents in the subject compositions is their high solubizing nature and ability to maintain and/or reduce unwanted ionization of the peptide. Of specific interest is N-methyl-2-pyrrolidone. N-methyl-2-pyrrolidone (NMP, Pharmasolve) is a very strong solubilizing agent and found as a solubilizing agent in a few commercially available pharmaceutical products. It is also found as a volatile component in roasted nuts, and is a versatile solvent miscible with water, ethyl alcohol, ether, chloroform, benzene, ethyl acetate and carbon disulfide.

In certain embodiments, the organic solvent includes a non-ionic surfactant. The non-ionic surfactant can also be a non-aqueous solvent, an organic solvent, and/or a water soluble organic solvent. Examples of the non-ionic surfactant include, but are not limited to, polyoxyl 35 castor oil (Cremophor EL), polyoxyl 40 hydrogenated castor oil (Cremophor RH 40), and polyoxyl 60 hydrogenated castor oil (Cremophor RH 60), as well as d-α-tocopherol, polyethylene glycol 1000 succinate, polysorbate 20, polysorbate 80, Sorbitan-monolaurate (Span 20), Sorbitan monopalmitate (Span 40); Sorbitan monostearate (Span 60); Sorbitan-monooleate (Span 80), Solutol HS 15, sorbitan monooleate, poloxamer 407, Labrafil M-1944CS, Labrafil M-2125CS, Labrasol, Gellucire 44/14, Softigen 767, and mono- and di-fatty acid esters of PEG 300, 400, or 1750. Each of these components is commercially available, found in a number of pharmaceutical products, and generally regarded as safe for their intended uses. Thus, in certain embodiments, the non-ionic surfactant is selected from a polyoxyethylated polyol, a polyoxyethylated polyol esterified with fatty acids, and mixtures thereof.

In certain embodiments, the non-ionic surfactant is a polyoxyethylated polyol selected from the group consisting of polyoxyl 35 castor oil (Cremophor EL), polyoxyl 40 hydrogenated castor oil (Cremophor RH 40), polyoxyl 60 hydrogenated castor oil (Cremophor RH 60), and mixtures thereof, and the polyethoxylated polyol esterified with fatty acids is selected from the group consisting of polysorbate 20 (Tween 20), polysorbate 80 (Tween 80), and mixtures thereof. A featured embodiment is where the non-ionic surfactant is a polyoxyethylated polyol, such as a polyethoxylated castor oil, and in particular, polyoxyl 35 castor oil (Cremophor EL). Also of interest is vitamin E, such as d-α-tocopherol alone or in combination with other vitamin E compounds, as it includes a moderately acidic phenol group that may benefit the subject formulations.

As such, in certain embodiments, the non-aqueous hydrophobic vehicle is acidic, and at least one acylglycerol is a medium chain acylglycerol, at least one lipid comprises a short chain fatty acid and/or a medium chain fatty acid, and at least one water soluble organic solvent is a polar aprotic solvent. For example, in a specific embodiment, the medium chain acylglycerol is mono-decanoyl glycerol, the short chain fatty acid is nonanoic acid, the medium chain fatty acid is oleic acid, and the polar aprotic solvent is N-methyl-2-pyrrolidone.

In other embodiments, the non-aqueous hydrophobic vehicle is neutral, and at least one acylglycerol is a medium chain acylglycerol, at least one lipid is a neutral lipid, and at least one water soluble organic solvent is a polar aprotic solvent. For example, the medium chain acylglycerol is a mixture of mono-decanoyl glycerol and octanoyl glycerol, the neutral lipid is vitamin E, and the polar aprotic solvent is propylene glycol N-methyl-2-pyrrolidone.

In some embodiments, the mucosal delivery composition is comprised as an emulsion, dispersion, liposome, or micelle, including a reverse micelle (as described in more detail below).

Other Components

The compositions may further comprise other pharmaceutically acceptable components as excipients. Examples of such components are well known in the art and include non-ionic surfactants, antioxidants, buffers, viscosity modifying agents, chelating agents, various types of wetting agents, dilutants, sterile solutions, and so forth (as described in more detail below).

Non-ionic surfactants or detergents include organic compounds having a hydrophobic tail and an uncharged head group. Examples include, but are not limited to, alkyl poly(ethylene oxide), alkylphenol poly(ethylene oxide), copolymers of poly(ethylene oxide) and poly(propylene oxide) (commercially called poloxamers or poloxamines), alkyl polyglucosides such as octyl glucoside and decyl maltoside, fatty alcohols such as cetyl alcohol and oleyl alcohol, cocamide MEA, cocamide DEA, and polysorbates such as Tween 20, Tween 80, and dodecyl dimethylamine oxide, and the like. Of specific interest are non-ionic detergents such as beta-D-octylglucoside.

Of particular interest are antioxidants, which are generally reducing agents such as thiols, melatonin, lipoic acid, uric acid, carotenes, ascorbic acid, polyphenols and the like, such as glutathione, and vitamin E, as well as enzymes such as catalase, superoxide dismutase and various peroxidases. Examples of antioxidants of specific interest include, but are not limited to, N-acetyl-methionine, biotin, ascorbic acid, glutathione, and vitamin E. As such, in one embodiment, the mucosal delivery composition comprises an antioxidant. In a related embodiment, the preformed peptide complex comprises an antioxidant.

Other components of particular interest are ascorbic acid alkanoate esters, the alkyl chain thereof preferably being from C8 to C24 and being saturated or unsaturated. Such compounds may act as surfactant. As such, they may promote microemulsion and formation of microgels. Preferred compounds falling into this class such as 6-O-lauryl ascorbic acid as described in Zaino et al., Lat. Am. J. Pharm., 28, 438-442, 2009. An advantage of ascorbic acid alkanoate esters is that they serve not only to deliver and stabilize the peptide active agent according to the present invention, but furthermore are capable of preventing or reducing oxidation thereof. Accordingly, these compounds may serve as surfactants and/or antioxidants.

Preferred carriers for mucosal delivery or diluents for formulation according to the disclosure include the non-aqueous solvents as discussed above. Compositions comprising such carriers can be formulated by well known conventional methods, taking into account the storage and dosage regimen, which can be determined by the clinical factors. For example, the peptide active agent may be present in amounts between 1 ng and 10 mg/kg body weight per dose; however, doses below or above this exemplary range are envisioned, especially considering the aforementioned factors. Envisaged formulations furthermore comprise microspheres, liposomes, microcapsules, and nanoparticles/nanocapsules.

Additional envisaged constituents of the compositions of to the disclosure include cyclodextrins (see, for example, Irie and Uekama (1999) or Challa et al. (2005)) and/or chitosan. Cyclodextrins form inclusion complexes with hydrophobic moieties present on a compound. Furthermore, they present a hydrophilic exterior surface. Compositions comprising cyclodextrins or chitosan may provide for a delayed release and/or a release over an extended period of time of the peptide active agent. Accordingly, compositions to be manufactured further comprises a cyclodextrins. Cyclodextrins are known in the art and include alpha-cyclodextrin, beta-cyclodextrin and gammacyclodextrin. In other words, the stably hydrated peptide active agent is in a first step complexed to form a first peptide complex, and then, in second step, the first peptide complex is complexed, to form a second layer, with cyclodextrines, more specifically be the hydrophobic inner cavity of cyclodextrins, thereby generating in total two levels of complexations. This opens possibilities to design novel delivery approaches: for examples, entrapping the stably active peptide ingredient into (i) liposomes, (ii) microspheres, (iii) microcapsules, (iv) nanoparticles/nanocapsules.

Excipients may further include one or more chelators, which may also serve as an antioxidant, counter ion, and/or buffering agent and the like, depending on the particular compound. Examples of such chelators include, but are not limited to, citric acid, phosphonates, antibiotics such as those of the tetracycline family, acrylic polymers, ascorbic acid, tetrasodium iminodisuccinate), dicarboxymethylglutamic acid, ethylenediaminedisuccinic acid (EDDS), ethylenediaminetetraacetic acid (EDTA), hepta sodium salt of diethylene triamine penta (methylene phosphonic acid) (DTPMP.Na$_7$), malic acid, nitrilotriacetic acid (NTA), non-polar amino acids (e.g., methionine and derivatives thereof), oxalic acid, phosphoric acid, polar amino acids (e.g., arginine, asparagine, aspartic acid, glutamic acid, glutamine, lysine, and ornithine, and derivatives thereof), siderophores such as desferrioxamine B, and succinic acid.

Buffers, such as sodium phosphate, TRIS, glycine, maleic acid, and sodium citrate, are examples of additional excipients that may be included to reduce the tendency of pH of the composition to change over time as would otherwise occur due to chemical reactions. In addition, one or more preservatives can be included to prevent or delay microbial activity (growth and metabolism). Examples of pharmaceutically acceptable preservatives are phenol, m-cresol and a mixture of phenol and m-cresol, benzoate and derivatives thereof, and the like.

Of course isotonic agents in general represent a broad category of excipients, and may include, for example, a salt (e.g. sodium chloride), a sugar or sugar alcohol (i.e., a $C_4$-$C_8$ hydrocarbon having at least one —OH group and includes, for example, mannitol, sorbitol, inositol, galactitol, dulcitol, xylitol, and arabito), an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Isotonic agents also include any sugar such as mono-,10 di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na.

The excipients such as those mentioned above may be used individually or in combination. There is no fixed limit to the amount used, as long as the excipient is soluble in the preparation and does not adversely affect the mucosal delivery composition or its components for a given end use. For convenience reference is made to Remington: The Science and Practice of Pharmacy, 19th edition, 1995.

Storage Stability

In certain embodiments, the subject mucosal delivery compositions and substituent components are prepared as storage stable preparations. In one embodiment, the mucosal delivery composition, and/or pharmaceutical and/or diagnostic preparations comprising the mucosal delivery composition, is storage stable. In one embodiment, the preformed peptide complex is storage stable. In a related embodiment, the non-aqueous hydrophobic vehicle is storage stable.

The term "storage stable" refers to compositions prepared for storage, aliquoting and/or shipping as separate and/or combined components, such as for inclusion in a kit, and particularly as a pharmaceutical and/or diagnostic formulation, which include a peptide active agent as an active ingredient, and in which the concentration of the active ingredient is effectively maintained during storage stability testing, and degradation products, oxidation products, and/or impurities which are typically observed in storage stability testing of such formulations are absent or significantly reduced during storage stability testing.

In one embodiment, storage stability is determined at a temperature range from about –20° C. to about 80° C., about 4° C. to about 70° C., about 4° C. to about 60° C., about 4° C. to about 50° C., about 4° C. to about 40° C., or about 4° C. to about 30° C. In another embodiment, storage stability is determined at a relative humidity ("RH") range of greater than about 1 to 5% RH, generally from about 10% RH to about 90% RH, about 20% RH to about 65% RH, or about 30% RH to about 75% RH. In an additional embodiment, storage stability is determined under inert gas, such as nitrogen, argon, and the like. Of particular interest are time intervals for measuring storage stability that range, for example, from about 1 week to 5 years, from about 2 weeks to about 4 months, or at intervals of 2 weeks, 4 weeks, 8 weeks, 12 weeks, 16 weeks, 6 months, and 12 months. In general, storage stability of a given composition is determinative when the composition is stored under the desired conditions suitable for a given end use, and stable for a period of about or greater than about 3 to 6 months, typically about 1 year or greater.

Storage stability can be assessed by various techniques well known in the art. For example, storage stability can be measured qualitatively and/or quantitatively, directly and/or indirectly, by various techniques known in the art, such as by chromatography (e.g., HPLC, Mass-Spectrophotometry etc.), enzymatically (measuring substrate consumption and/or modification, or product and/or by-product production), antigen-antibody binding (e.g., Western Blot, Enzyme-Linked ImmunoSorbent Assay (ELISA) etc.), by biological effect (e.g., pharmacological bioavailability by indirect measure of amount of the peptide active agent that enters the blood stream, such as illustrated in the experimental section below), and the like.

Storage stable pharmaceutical and/or diagnostic formulations of the subject disclosure include those which maintain the initial concentration of the peptide active agent at a level that meets or exceeds The United States Food and Drug Administration (FDA) regulatory standards for peptide pharmaceuticals. As such, specific formulations of the disclosure maintain the initial concentration of the peptide active agent for a period of greater than about 6 months, and in certain embodiments, for a period of greater than about 12 months, including up to about 2 years, while the average impurity concentration is less than about 1%, typically less than about 0.1%. Also, within each respective period of time, the mucosal delivery activity in specific embodiments is reduced by 10% at the most, and the pharmacokinetic and/or pharmacological parameters do not show any substantial change.

Formulations

In certain embodiments, the peptide complex and/or peptide salt and the non-aqueous hydrophobic vehicle are combined into a single composition that is administered to the host. In yet other embodiments, the peptide complex and/or peptide salt and non-aqueous hydrophobic vehicle are each individually provided in separate compositions for subsequent combination into a single composition that is administered to the host. In additional embodiments, the peptide salt in the non-aqueous hydrophobic vehicle and/or the crown compound are each individually provided in separate compositions for subsequent combination into a single composition that is administered to the host. Thus, the peptide complex and/or peptide salt and non-aqueous hydrophobic vehicle can be provided in a single composition, or provided each individually in separate compositions, and various combinations thereof, including in separate reservoirs of a dosage form or device, for subsequent combination as part of a delivery system of the disclosure, or any effective variation thereof.

Whether the peptide complex and/or peptide salt is preformed ex situ or assembled in situ, for mucosal delivery the peptide complex and/or peptide salt and the other mucosal delivery composition components are each individually combined in an effective amount, i.e., a biologically relevant amounts. Generally, the peptide active agent comprises about 0.001-10% by weight of the mucosal delivery composition, usually about 0.01-5%, about 0.01-3%, and more generally about 0.01-2%, with the balance being the remaining components of the mucosal delivery composition.

Thus the components of the subject mucosal delivery composition are combined in amounts for mucosal delivery of an effective amount of the peptide active agent. Such compositions therefore comprise effective mixtures of their constituent components suitable for this purpose and corresponding given end use.

The mucosal delivery composition in general comprises an effective mixture of about 0.1-50% by weight peptide complex or peptide salt, and about 50-99.9% by weight non-aqueous hydrophobic vehicle, balance being substantially one or more additional pharmaceutically acceptable excipients.

A particular aspect is where the non-aqueous hydrophobic vehicle comprises at least one acylglycerol, at least one organic solvent such as a water soluble organic solvent, and optionally at least one lipid. Under these premises, the peptide, dried or lyophilized at the desired pH with the counter ions of choice, can be dissolved or suspended in the organic solvent, 1% to 50% v/v to the final mixture composition, more precisely 3% to 25%, 5% to 20%, 6% to 15% v/v to the final mixture composition, optionally with water 0.1% to 15% v/v to the organic solvent and the crown structure. Then after peptide dissolution in the first organic solvent, the acylglycerol is added with optionally the second organic solvent (non-ionic surfactant) and optionally the lipid.

A featured aspect is where the non-aqueous hydrophobic vehicle comprises at least one acylglycerol, at least one lipid, and optionally, at least one organic solvent, such as a water soluble organic solvent. The acylglycerol comprises up to about 80% by weight of the mucosal delivery composition, such as about 20-80%, about 30-70%, about 40-60%, and generally about 45-55%. The lipid component comprises about 5-60% by weight of the mucosal delivery composition, such as about 10-50%, usually about 20-40%. When present, the organic solvent comprises about 1-50% by weight of the mucosal delivery composition, usually about 5-30%, and typically about 5-10%, depending on the organic solvent or system.

In one embodiment, the mucosal delivery composition comprises an effective mixture of about 0.1-20% by weight peptide complex or peptide salt, about 35-55% by weight acylglycerol, and about 30-50% by weight lipid, balance being substantially one or more additional pharmaceutically acceptable excipients.

In some embodiments, the mucosal delivery composition comprises an effective mixture of about 0.1-15% by weight peptide complex or peptide salt, about 45-55% by weight acylglycerol, and about 30-45% by weight lipid, balance being substantially one or more additional pharmaceutically acceptable excipients, where the acylglycerol is selected from a monoacylglycerol, diacylglycerol, and mixtures thereof, and the lipid is a permeability-enhancing lipid selected from a neutral lipid, a charged lipid, or a mixture thereof. Of specific interest is where the acylglycerol is a monoacylglycerol such as mono-decanoyl glycerol and/or octanoyl glycerol, and the permeability-enhancing lipid comprises a mixture of short chain and medium chain saturated or unsaturated fatty acids having 7-19 carbon atoms such as nonanoic acid and oleic acid, and/or comprises a neutral lipid such as vitamin E.

In certain embodiments, the mucosal delivery composition comprises an effective mixture of about 0.1-15% by weight peptide complex or peptide salt, about 35-55% by weight acylglycerol, about 30-45% by weight lipid, and about 5-15% by weight water-soluble organic solvent, balance being substantially one or more additional pharmaceutically acceptable excipients. A featured aspect is where the acylglycerol is selected from a monoacylglycerol, a diacylglycerol, or mixtures thereof, the lipid is a permeability-enhancing lipid selected from a neutral lipid, a charged lipid, or mixtures thereof, and the water-soluble organic solvent is selected from a polar solvent, and a polar aprotic solvent. Of specific interest is where the acylglycerol is a monoacylglycerol such as mono-decanoyl glycerol and/or octanoyl glycerol, the permeability-enhancing lipid comprises a mixture of short chain and medium chain fatty acids such as nonanoic acid and oleic acid, or comprises a neutral lipid such as vitamin E, and where the water-soluble organic solvent comprises polar solvent such as a diol or polyol, or a polar aprotic solvent such as N-methylpyrrolidone.

In certain embodiments, the mucosal delivery composition comprises an effective mixture of about 0.1-15% by weight peptide complex or peptide salt, about 35-45% by weight water-soluble organic solvent, and about 35-55% by weight acylglycerol, balance being substantially a non-ionic surfactant and optionally one or more additional pharmaceutically acceptable excipients, where the water-soluble organic solvent comprises a mixture of a diol and a polyol, and the acylglycerol is a monoacylglycerol. Of specific interest is such a composition where the diol is glycerol, the polyol is propylene glycol, and the monoacylglycerol is mono-decanoyl-glycerol and/or octanoyl glycerol. Also of specific interest is such a composition where the non-ionic surfactant comprises about 10-30% by weight of the mucosal delivery composition, and wherein the non-ionic surfactant comprises a polyoxyethylated polyol. A particular polyoxyethylated polyol of interest is polyoxyl 35 castor oil (Cremophor EL).

In other embodiments, the mucosal delivery composition comprises an effective mixture of about 0.1-15% by weight peptide complex or peptide salt, about 5-25% by weight water-soluble organic solvent, and about 45-55% by weight acylglycerol, balance being substantially a non-ionic surfactant, a permeability-enhancing fatty acid, and optionally one or more additional pharmaceutically acceptable excipients, and wherein the water-soluble organic solvent is a polar aprotic solvent that optionally includes polyethylene glycol, and the acylglycerol is a monoacylglycerol. Of particular interest is such a composition wherein the polar aprotic solvent is N-methylpyrrolidone, the monoacylglycerol is a medium chain monoacylglycerol such as mono-decanoyl-glycerol and/or octanoyl glycerol, and the polyethylene glycol is a short chain polyethylene glycol diol, such as a polyethylene glycol diol selected from hexaethylene glycol, PEG 300, PEG 400, and mixtures thereof. Of further interest is such a composition where the non-ionic surfactant comprises about 10-30% by weight of the mucosal delivery composition, and wherein the non-ionic surfactant comprises a polyoxyethylated polyol, such as polyoxyl 35 castor oil (Cremophor EL).

Also of interest is a mucosal delivery composition that comprises an effective mixture of about 0.1-15% by weight peptide complex or peptide salt, about 5-25% by weight water-soluble organic solvent, about 45-55% by weight acylglycerol, about 15-25% by weight permeability-enhancing fatty acid, about 10-30% by weight non-ionic surfactant; balance being optionally one or more additional pharmaceutically acceptable excipients, and wherein the water-soluble organic solvent is a polar aprotic solvent that optionally includes polyethylene glycol, the acylglycerol is a monoacylglycerol, the non-ionic surfactant comprises a polyoxyethylated polyol, and wherein the permeability-enhancing fatty acid is a saturated or unsaturated fatty acid having 7-19 carbon atoms.

Of specific interest are such compositions in which the polar aprotic solvent is N-methylpyrrolidone, the monoacylglycerol is a medium chain monoacylglycerol such as mono-decanoyl-glycerol and/or octanoyl glycerol, the polyethylene glycol is a short chain polyethylene glycol diol (such as hexaethylene glycol, PEG 300, PEG 400, and mixtures thereof), the non-ionic surfactant comprises a polyoxyethylated polyol (such as polyoxyl 35 castor oil (Cremophor EL)), and the permeability-enhancing fatty acid is a saturated fatty acid selected from caprylic acid, octanoic acid, nonanoic acid, decanoic acid, undecanoic acid, dodecanoic acid, myristic acid, palmitic acid, stearic acid, arachidic acid, and mixtures thereof, and/or a an unsaturated fatty acid selected from palmitoleic acid, oleic acid, linoleic acid, alpha-linoleic acid, and mixtures thereof. A featured aspect are such compositions in which the permeability-enhancing fatty acid is a saturated fatty acid having 7-12 carbon atoms selected from caprylic acid, octanoic acid, nonanoic acid, decanoic acid, undecanoic acid, dodecanoic acid, and mixtures thereof. A particular embodiment is such a composition where the permeability-enhancing fatty acid is nonanoic acid.

To maximize the benefits of the compositions, there are mixtures that are particularly preferred for certain embodiments of the present disclosure. For example, if the water-soluble organic solvent is composed primarily of acylglycerol, a featured composition comprises a non-aqueous hydrophobic vehicle that is a combination of a monoacylglycerol such as mono-decanoyl-glycerol and/or octanoyl glycerol, a mixture of saturated or unsaturated permeability enhancing fatty acids having 7-21 or 7-19 carbon atoms such as nonionic and oleic acid, and a polar aprotic solvent such as N-methyl-2-pyrrolidone. If the water-soluble organic solvent is composed primarily of humectant, a featured composition comprises a non-aqueous hydrophobic vehicle that is a combination of glycerol, propylene glycol, a monoacylglycerol such as mono-decanoyl-glycerol and/or octanoyl glycerol, a polyethoxylated polyol such as polyoxyethylated 35 castor oil (Cremophor EL), and optionally a short chain PEG diol such as hexaethylene glycol, PEG 300 or PEG 400. If the water-soluble organic solvent is composed primarily of polar aprotic solvent, a featured composition comprises a non-aqueous hydrophobic vehicle that is a combination of N-methyl-2-pyrrolidone, a monoacylglycerol such as mono-decanoyl-glycerol and/or octanoyl glycerol, a polyethoxylated polyol such as polyoxyethylated 35 castor oil (Cremophor EL), a medium chain saturated fatty acid such as nonanoic acid, and optionally a short chain PEG diol such as hexaethylene glycol, PEG 300 or PEG 400. Further by way of example, a featured aspect is where the peptide active agent in the above formulations is human insulin, exendin-4, or liraglutide (or pharmaceutically acceptable analogues/derivatives thereof), and the composition further comprises an antioxidant such as N-acetyl-methionine, and preferably a buffer.

A preferred organic solvent to be used for the compositions of the invention is a polyol. Preferred polyols are propylene glycol and glycerol or a mixture of the two. Indeed, the Log P of the propylene glycol and glycerol are both negative and about in the range of the water, thus being a preferred replacement for water. The addition of the further constituents of the vehicle of the invention, said further constituents comprising or consisting of mono acyl glycerols and optionally fatty acid lipids and optionally a non ionic surfactant mixture with final positive Log P about or above 1.5, preferably above 2, surprisingly allows enhanced peptide solubilization, superior stabilization, and improved delivery through mucosa. Accordingly, addition of the polyol and of the further constituents of the vehicle is preferably effected subsequently; see also Formulation 1a as described in the Examples section.

To maximize the benefits of these compositions, the stably hydrated peptide active agent is complexed with (i) a crown compound selected from an 18-crown-6 and oxo crown analogues/derivatives thereof, and (ii) a counter ion selected from salicylic acid, acetic acid, phosphate, sodium, potassium, N-acetyl-lysine-amide, N-acetyl-arginine-amide, and mixtures thereof, wherein the pH of the composition is different from the isoelectric point of the peptide active agent, particularly where the pH of the composition is remote from the isoelectric point of the peptide active agent, and more particularly where the composition includes a buffer. Salicylic acid and acetic acid are of specific interest for many embodiments. The level of each component that makes up these mixtures is described in detail above, and in the experimental section below, and partially dependent on benefits sought by the formulator, and thus may also beneficially include one or more additional pharmaceutically acceptable excipients.

The subject compositions described above can be used directly or adapted in other dosage forms for mucosal administration for use in the subject methods. Thus, the compositions can be dosed in a variety of product forms and, or package delivery options. The compositions of the present disclosure provide improved activity while minimizing potential side effects. For example, to take advantage of the benefits of the compositions of the present disclosure, the stably hydrated peptide active agent is typically in complex with a crown compound and/or a counter ion, however, the free form of the stably hydrated peptide active agent is also useful in the present disclosure. Regardless of its form, the mucosal delivery compositions of the disclosure contain the stably hydrated peptide active agent in an essentially non-aggregated and non-oxidized form.

Another consideration is that a particular non-aqueous hydrophobic vehicle of interest is normally a semi-solid, gel or liquid at ambient or room temperatures based on the selection of the components of the composition described above. Accordingly, there are mixtures of these components that are particularly preferred for certain embodiments of the present disclosure. For example, compositions comprising a non-aqueous hydrophobic vehicle composed of a mixture of an acylglycerol, fatty acids, and a water soluble organic solvent, are provided that have different melting points. As such, the mucosal delivery composition can be readily provided as a liquid or as a gel or solid dosage form designed to dissolve in the mouth of mammal.

For instance, a non-aqueous hydrophobic vehicle of specific interest comprises about 8% by weight NMP, about 50% by weight mono-decanoyl glycerol, about 20% by weight nonanoic acid, and about 15% by weight oleic acid. This mixture is a solid at 19-20° C., definitely a liquid a 38-40° C., but soft or beginning to melt at 25-30° C. A solid formulation of this composition can be made by exposure to a cold plate or mold, where the liquid is placed in well on the cold plate to solidify and form a pill structure. When placed in the mouth of a mammal, it melts in about 1 minute. However, to prepare a solid formulation that is solid at 25° C., but starts melting at about 35-40° C., the formulation can be adjusted to increase percentage of mono-dodecanol glycerol (10-15% more to increase melting temp by about 2-3° C.) to increase melting temperature of the formulation. Also, since nonanoic acid is liquid whereas decanoic acid is solid at room temperature, and oleic acid is liquid at room temperature and solid at 4° C., to prepare a solid formulation that is solid at 25° C., but starts melting at about 35-40° C., the length of the fatty acid can be increased, e.g., add or substitute decanoic acid for nonanoic to form a mucosal delivery composition having a melting point of about 35° C. to 40° C. Thus, formulation of the non-aqueous hydrophobic vehicle is afforded great flexibility in terms of dosage form design when employed in combination with a stably hydrated peptide complex of the disclosure.

As also described above, in certain embodiments, the mucosal delivery composition is a pharmaceutical and/or diagnostic composition which may include one or more additional pharmaceutically acceptable excipients, with the proviso that such excipients are compatible with maintaining the peptide complex. Pharmaceutically and/or diagnostically acceptable excipients are also well-known to those who are skilled in the art and are readily available. The choice of excipient will be determined in part by the particular composition, as well as by the particular method used to administer the composition. Accordingly, there are a wide variety of suitable formulations of the pharmaceutical and/or diagnostic compositions of the present disclosure.

By way of illustration, the peptide complex or peptide salt combined with the non-aqueous hydrophobic vehicle can be used alone (i.e., 100% by weight of the pharmaceutical and/or diagnostic composition), or admixed with conventional pharmaceutically and/or diagnostically acceptable carriers and excipients if desired and used in the form of solutions, tablets, capsules, elixirs, suspensions, syrups, wafers, and the like. Such pharmaceutical compositions contain, in certain embodiments, up to about 99.975% by weight of the peptide complex combined with the non-aqueous hydrophobic vehicle, depending on the dosage form and intended end use. For example, in some embodiments, the pharmaceutical and/or diagnostic composition will generally contain from about 0.001 to 10% of the stably hydrated peptide active agent, typically about 0.05% to 5% of the stably hydrated peptide active agent, usually about 0.01 to 3% of the stably hydrated peptide active agent, and more generally, about 0.1% to 2% of the stably hydrated peptide active agent for a given unit dose. Thus, the peptide complex combined with the non-aqueous hydrophobic vehicle of the present disclosure will comprise from about 60% to about 99.975%, usually from 70% to about 99% and most often from about 85% to about 98% by weight of the pharmaceutical composition.

The pharmaceutical and/or diagnostic compositions may be administered alone or as part of a drug delivery system that maintains the peptide formulation in a drug transferring relationship with a target mucosal membrane, such as an oral mucosal membrane like a buccal membrane and/or sublingual membrane. As such, the peptide formulation can be in a free form, such as a liquid, gel, cream, foam, ointment, or semi-solid, or can comprise a device of determined physical form, such as spray, tablets, patches, and troches, for example, as described in U.S. Pat. Nos. 4,226,848; 4,250,163; 4,292,299; 4,517,173; 4,552,751; 4,572,832; 4,615,697; 4,713,243; 4,900,554; 4,915,948; 5,047,244; 5,081,157; 5,081,158; 5,137,729; 5,192,802; 5,298,258; 5,314,915; 5,458,879; 5,462,749; 5,578,315; 5,624,677; 5,750,134; 5,750,136; 5,766,620; 5,780,045; 5,800,832; 5,827,525; 5,849,322; 5,855,908; 5,861,174; 5,863,555; 5,869,082; 5,888,534; 5,908,637; 5,955,097; 5,955,098; 6,103,226; 6,103,266; 6,110,486; 6,117,446; and 6,159,498; which disclosures are incorporated herein by reference.

In certain embodiments of interest, the pharmaceutical and/or diagnostic compositions of the disclosure may also be used in combination with other active agents as excipients in this context, including incorporation of the peptide active agent with a non-peptide active agent, or two or more peptide active agents, and so forth, in the same composition.

It will also be appreciated that the pharmaceutical and/or diagnostic compositions of the disclosure may find more beneficial use for specific routes of administration involving mucosal surfaces, including oral mucosal membranes, airway surfaces, gut and the like. For example, in certain embodiments, pharmaceutical compositions for oral mucosal delivery are of specific interest, particularly pharmaceutical compositions for buccal and/or sublingual delivery. Thus, pharmaceutical and/or diagnostic compositions of the disclosure that comprise a stably hydrated peptide active agent in an oral mucosal delivery vehicle are of particular interest.

One skilled in the art will appreciate that a variety of suitable methods of administering a formulation of the present disclosure to a subject or host, e.g., patient, in need thereof, are available, and, although more than one route can be used to administer a particular formulation, a particular route can provide a more immediate and more effective reaction than another route (e.g., buccal spray versus sublingual gel). Thus, the pharmaceutical and/or diagnostic composition may optionally contain other pharmaceutically and/or diagnostically acceptable components, such a buffers, surfactants, antioxidants, bacteriostats, viscosity modifying agents, suspending agents, solubilizers, stabilizers preservatives and the like. Each of these components is well-known in the art. For example, see U.S. Pat. Nos. 6,193,997; 6,214,375; 6,221,378; 6,231,882; 6,271,200; 6,290,987; 6,294,153; 6,312,665; 6,315,984; 6,350,432; 6,350,458; 6,375,975; 6,432,383; 6,436,367; 6,451,286; 7,070,799; 7,087,215; 7,115,561; and 7,255,102; the disclosures of which is herein incorporated by reference. Other components suitable for use in the formulations of the present disclosure can be found in Remington: The Science and Practice of Pharmacy, 19th edition, 1995.

The formulations can be presented in unit-dose or multi-dose sealed containers, such as ampules and vials, spray containers, tablets and the like, or can be stored in a freeze-dried (lyophilized) condition requiring only the addition of a suitable sterile liquid excipient immediately prior to use. Extemporaneous solutions and suspensions can be prepared from sterile powders, granules, and tablets of the kind previously described. For instance, unit dosage forms for oral administration such as semi-solids, gels, syrups, elixirs, tablets and suspensions may be provided wherein each dosage unit, for example, teaspoonful, tablespoonful, or tablet, contains a predetermined amount of the composition containing the peptide active agent in the mucosal delivery vehicle.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host.

Those of skill in the art will readily appreciate that dose levels can vary as a function of the specific compound, the nature of the delivery vehicle, and the like. Suitable dosages for a given compound are readily determinable by those of skill in the art by a variety of means.

The dose administered to an animal, particularly a human, in the context of the present disclosure should be sufficient to cause a prophylactic or therapeutic response in the animal over a reasonable time frame. One skilled in the art will recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Suitable doses and dosage regimens can be determined by comparisons to agents that are known to cause the desired response.

In certain embodiments, the mucosal delivery composition is comprised as a dosage form selected from the group consisting of buccal, sublingual, and a combination thereof.

Applications

The subject methods find use in a variety of applications. Examples include as reagents, diagnostics, and pharmaceutical agents for treatment of a host of interest. In certain embodiments, the methods of treatment involve administering a composition of the disclosure to a mucosal membrane of a host in need thereof, such as for the treatment of a host suffering from disease or condition treatable by a peptide active agent. An aspect of the subject methods is that an effective amount of the composition is administered to deliver an effective amount of the peptide active agent into the blood stream of the host. In a featured embodiment, the mucosal delivery composition is an oral mucosal delivery composition, and the mucosal membrane is an oral mucosal membrane.

Also provided is a method of mucosal delivery of an effective amount of a peptide active agent to a host in need thereof, the method comprising: administering to a mucosal membrane of the host an effective amount of a mucosal delivery composition and/or peptide complex of the disclosure, wherein the administering delivers an effective amount of the peptide active agent into the blood stream of the host. In certain embodiments, the mucosal membrane is an oral mucosal membrane, such as an oral mucosal membrane selected from the group consisting of buccal, sublingual, and combinations thereof. Of specific interest is where sublingual administration of the composition results in a pharmacological bioavailability of the peptide active agent that is greater than about 10%, preferably greater than about 15%, and more preferably about 20% or greater, relative to intrapleural (pI) administration.

As described above, the peptide active agent is generally one that is capable of mucosal delivery in the subject formulations. In certain applications, the methods are methods of modulating at least one cellular function associated with the peptide active agent. In this respect, the subject methods and compositions find use in known applications of many peptide active agents, such as in treating diseases or disorders that are capable of being treated using the peptide active agent. Use of the subject compositions of the present disclosure is of particular utility in, for example, the treatment of diseases and disorders where a gradual (e.g., gastrointestinal mucosal delivery) or rapid (e.g., oral mucosal delivery) onset of effect is desired, without the need for injection.

As such, the subject methods and compositions find particular use in therapeutic applications in which administration of a given peptide active agent is indicated. In many embodiments, the peptide active agent is a peptide hormone, such as insulin, calcitonin, parathyroid hormone, an incretin mimetic peptide such as a glucagon-like peptide, and the like. A representative therapeutic application is in the treatment of diabetes, obesity and related conditions using a composition of the disclosure in which the peptide active agent is, for instance, insulin, and/or an incretin mimetic peptide, such as exendin-4 or liraglutide.

By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition.

A specific application of interest is the use of peptide active agents in the mucosal delivery vehicle compositions of the disclosure, particularly insulin, exendin-4, glucagon-like peptide 1, liraglutide, and analogues/derivatives thereof, to decrease blood glucose levels in the host. In a related embodiment, the condition is type II diabetes. Another specific application of interest is the use of peptide active agents in the mucosal delivery vehicle compositions of the disclosure, particularly exendin-4, liraglutide, and analogues/derivatives thereof, for the reduction of the weight of the host. Thus, in certain embodiments, a method is provided for the treatment of a host in need thereof an effective amount of a pharmaceutical agent of the disclosure that comprises a peptide active agent selected from insulin, exendin-4, liraglutide, glucagon-like peptide 1, and analogues/derivatives thereof.

Reduction of blood glucose levels is characterized by the prevention, mitigation, or reduction of the likelihood of onset of hyperglycemia resulting from elevated blood glucose levels. Reduction of weight is characterized by the prevention, mitigation, or reduction of the likelihood of onset of obesity or weight gain resulting from one or more of elevated blood glucose levels, gastric emptying, and food intake. This includes, for example, treatment of a host in need thereof with an effective amount of an GLP active agent in an mucosal delivery vehicle of the disclosure to reduce blood glucose levels, delay gastric emptying, and/or decrease food intake in the host. By "GLP active agent" is intended exendin-4, liraglutide, and pharmaceutically acceptable analogues/derivatives thereof.

For example, hyperglycemia can easily be assessed by standard techniques known in the art, such as by measuring blood glucose levels. Likewise, gastric emptying, decrease in food intake, and the weight of a host can be readily determined. Thus, the effect of treatment with the GLP active agent can readily be determined using any, or all, of these test systems.

A variety of hosts (or subjects) are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects will be humans.

In certain embodiments, the hosts will be subjects that have been diagnosed for and are, therefore, in need of administration of the active agent. In certain embodiments, the methods may include diagnosing the subject for the presence of the disease condition to be treated by administration of the peptide active agent.

As noted above, the dose administered to an animal, particularly a human, in the context of the present disclosure should be sufficient to affect a prophylactic or therapeutic response in the animal over a reasonable time frame. One skilled in the art will recognize that dosage will depend on a variety of factors including the strength of the particular peptide active agent employed, the dose of the peptide active agent, the dosing regimen used for peptide active agent, the condition of the animal, and the body weight of the animal, as well as the severity of the illness and the stage of the disease.

The size of the dose will also be determined by the existence, nature, and extent of any adverse side-effects that might accompany the administration of a particular peptide active agent. This will generally follow the dose and dosing profile for treatment of a condition for which the peptide active agent is indicated and/or empirically determined following routine methods.

In the treatment of some individuals with the compounds of the present disclosure, it may be desirable to use a high dose regimen in conjunction with standard therapies. For example, exendin-4 and liraglutide can be used in combination with metformin, a sulfonylurea, or a thiazolidinedione, as well as in conjunction with standard insulin therapy to manage blood glucose levels for type II diabetes. Such treatment regiments are well known to those of ordinary skill in the art.

A featured embodiment is the use of a mucosal delivery composition that is an oral mucosal delivery composition of the disclosure, and wherein the oral mucosal delivery composition comprises a peptide active agent selected from insulin, exendin-4, liraglutide, glucagon-like peptide 1, and analogues/derivatives thereof, for treatment of a host in need thereof, for instance, to treat one or more conditions described above for these compounds.

Particular applications in which the subject methods and compositions find use include those described in U.S. Pat. Nos. 5,118,666; 5,120,712; 5,187,154; 5,264,372; 5,376,637; 5,424,286; 5,512,549; 5,545,618; 5,552,520; 5,574,008; 5,614,492; 5,631,224; 5,686,511; 5,846,937; 5,958,909; 6,162,907; 6,191,102; 6,268,343; 6,284,727; 6,358,924; 6,448,045; 6,458,924; 6,506,724; 6,528,486; 6,703,359; 6,706,689; 6,723,530; 6,767,887; 6,828,303; 6,849,708; 6,852,690; 6,858,576; 6,872,700; 6,884,585; 6,899,883; 6,902,744; 6,911,324; 6,924,264; 6,956,026; 6,982,248; 6,989,148; 6,989,366; 7,022,674; 7,056,734; 7,056,887; 7,078,375; 7,084,243; 7,115,569; 7,119,168; 7,138,375; 7,138,486; 7,153,825; 7,157,555; 7,164,005; 7,220,721; 7,223,725; 7,226,990; 7,259,234; 7,273,850; 7,297,761; 7,307,148; the disclosures of which are herein incorporated by reference.

Kits & Systems

Also provided are kits and systems comprising one or more compositions of the present disclosure, as well as those that find use in practicing the subject methods, as described above. In one embodiment, the kit comprises an effective amount of a mucosal delivery composition, and/or components thereof that are each individually separate and/or provided in various combinations in the kit in effective amounts capable of forming the mucosal delivery composition upon combination. For example, in one embodiment the kit comprises: (i) a first composition comprising the stably hydrated peptide active agent complexed with the crown compound and the counter ion, and (ii) a second composition comprising the non-aqueous hydrophobic vehicle. In another embodiment, the kits comprises: (i) a first composition comprising the stably hydrated peptide active agent complexed with the counter ion in the non-aqueous hydrophobic vehicle, and (ii) a second composition comprising the crown compound. Other effective combinations are possible.

Kits and systems for practicing the subject methods may include one or more pharmaceutical and/or diagnostic formulations. As such, in certain embodiments the kits may include a single pharmaceutical and/or diagnostic composition, present as one or more unit dosages, where the composition includes the peptide active agent predisposed in the mucosal delivery composition. In other embodiments, the kits may include two or more separate pharmaceutical and/or diagnostic compositions, each containing either the stably hydrated peptide active agent in complex with the crown and counter ion, or non-aqueous hydrophobic composition, and any effective variation thereof. In a specific embodiment, the mucosal delivery composition employed in, or capable of being formed by, the kits and systems of the disclosure is an oral mucosal delivery composition.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits. For example, a kit according to one embodiment includes as a first component (a) instructions for using a pharmaceutical and/or diagnostic composition of the present disclosure, and as a second component (b) a pharmaceutical and/or diagnostic composition of the present disclosure.

Kits of specific interest are those that include a pharmaceutical and/or diagnostic composition of the disclosure and suitable for practicing the subject methods of the disclosure, such as for reducing blood glucose levels, delaying gastric emptying, and/or reducing food intake in a host.

The term "system" as employed herein refers to a collection of the components of a peptide formulation of the disclosure, present in a single or disparate composition, that are brought together for the purpose of practicing the subject methods. For example, separately obtained peptide or peptide forms brought together and admixed with a mucosal delivery vehicle or its components for administering to a host, according to the present disclosure, are a system according to the present disclosure.

The subject methods and compositions for peptide delivery directly through mucosal membranes offer advantages over other routes of administration. As noted above, a particular route of interest is via oral mucosal delivery. For example, drugs administered through oral mucosal membranes have a rapid onset of action, provide therapeutic plasma levels, avoid first pass effect of hepatic metabolism, and avoid exposure of the drug to the hostile GI environment. Additional advantages include easy access to the membrane sites so that the drug can be applied, localized and removed easily. Further, there is a good potential for prolonged delivery of large molecules through these membranes.

In addition, the oral mucosa in general has excellent accessibility, an expanse of smooth muscle, and a relatively immobile mucosa, and is hence suitable for the administration of retentive dosage forms. Direct access to the systemic circulation through the internal jugular vein allows drugs to bypass the hepatic first-pass metabolism, leading to high bioavailability. Other advantages include low enzymatic activity, suitability for drug excipients that mildly and reversibly damage or irritate the mucosa, painless administration, easy drug withdrawal, facility to include a permeation enhancer/enzyme inhibitor or pH modifier in the formulation, and versatility in the design of multidirectional or unidirectional release systems for local or systemic action. Thus, the mucosa lining the oral cavity represents an important topical route for the delivery of large therapeutic compounds such as peptides in accordance with the present disclosure.

The following examples illustrate the effective oral mucosal administration of representative peptide active agents of the disclosure, and illustrate the desired biological effect of the active peptide, including a constant, predictable drug concentration to the blood. Thus, administration of these and other peptides in accordance with the present disclosure by oral mucosal or other mucosal delivery routes may offer certain advantages over injection and other modes of administration including convenience and speed of delivery, as well as by reducing or elimination of compliance problems and side effects that attend delivery by injection.

Thus, the following examples further illustrate the present disclosure and should not be construed as in any way limiting its scope.

EXPERIMENTAL RESULTS

I. General Procedures for Preparation of Mucosal Delivery Formulations

Step 1: Alternative Peptide Solubility Improvement by Desalting

Peptides were optionally desalted by Reverse Phase High Performance Chromatography (RP-HPLC) (solvents were water and acetonitrile in the presence of 1% acetic acid) and lyophilized (i.e., freeze dried at less than room temperature). Depending on the pI of the molecule, the molecule is either utilized as it is in lyophilized form, or when required, re-dissolved or suspended in water or water/acetonitrile mixtures. The pH of the obtained solution or suspension was then brought to a desired value ranging from 4 to 7.5 such that the pH was sufficiently different from the pI of the molecule to insure solubility in various solvents employed in subsequent counter ion exchange and/or complexing reactions. For example, for glucagon-like peptides such as exendin-4 and liraglutide were prepared by the careful and/or gradual addition of a base to obtain the desired pH (e.g., sodium or potassium bicarbonate, amino acids as Lys or Arg and protected derivatives such as N-acetylated and/or amidated versions). When the desired pH was reached, the obtained solution or suspension was if necessary filtered through a 0.45 μm filter and lyophilized at this given pH ranging from 4 to 7.5. This treatment was found to be critical for further peptide solubility in various solvents or solvent mixtures (e.g., water/acetonitrile mixture, organic solvents as methanol or ethanol).

Stabilizing excipients such as mannitol may also be included in the solvent for RP-HPLC, and/or in the water/acetonitrile mixtures following RP-HPLC, provided the excipient(s) is added in an amount that dissolves in the mixture (typically 0, 1-20%).

Step 2: Alternative Counter Ion Exchange

Peptide counter ion (usually acetate counter ion) was alternatively substituted by acidic compounds such as salicylic acid, different substituted or not benzoic acid derivatives, oxalic acid, sulfonates, sulfates such as lauryl sulfate, phosphatidylglycerol derivatives such as dilaurylphosphatidyl glycerol (DLPG), phosphoric acid, trifluoroacetic acid or chloride. This counter ion exchange was found to affect protein/peptide solubility and/or in vivo activity.

For example, the peptide acetate was converted to salicylate salt by the following treatment. Salicylic acid (138.12 g/mol) was dissolved in ACN/$H_2O$ 50/50 mixture to give the mother solution. Fixed volume of this latter solution (containing fixed quantity of salicylic acid in a ratio of 1 to n equivalents regarding peptide/protein basic amino acid content) were added to peptide acetate dissolved in ACN/$H_2O$ 50/50. In some cases, a small amount of a non-ionic detergent such as beta-D-octylglucoside (0.05% to 10%, more preferably 0.1% to 5%), mannitol (10-20% final concentration in the formulation mixture), and/or glycerol (1% final concentration in the formulation mixture) were added to the mixture. The obtained solution was dried/concentrated for 1 hour using a centrifugal evaporator/SpeedVac (at 25° C.-40° C., typically around 35° C.), then ACN/$H_2O$ 50/50 was added and this solution dried/concentrated by SpeedVac (at 25° C.-40° C., typically around 35° C.) for an additional hour, affording peptide salicylate as a white solid.

Step 3: Preparation of the Peptide-Crown Compound Complex

The peptide salt was dissolved in MeOH or MeOH/$H_2O$ mixtures (water content ranging from 1 to 15%) and appropriate amount of cyclic crown compound dissolved in MeOH or MeOH/$H_2O$ mixtures added (containing fixed quantity of crown compound in a ratio of 1 to n equivalents regarding peptide/protein basic amino acid content). The obtained solution was dried/concentrated for 1 hour in a SpeedVac (at 25° C.-40° C., typically around 35° C.), to generate an oily residue comprising the peptide salt-crown compound complex. Alternatively, in some cases, an organic solvent (such as DMSO, NMP or propylene glycol) solution of crown compound was added to the dried peptide salt and the resulting mixture was incubated for about 10-15 minutes before addition of the formulation vehicle.

Step 4: Final Formulation Preparation

A viscous non-aqueous hydrophobic formulation vehicle was added to peptide-crown compound complex and the resulting mixture vortexed then heated at 40° C. for 10 minutes. The obtained limpid preparation was then stored at +4° C.

Formulation 1:

The formulation vehicle was prepared by adding NMP (20 μl), oleic acid (40 μl) followed by nonanoic acid (50 μl) to decanoyl glycerol (130 mg). The obtained mixture was heated at 40-45° C. in a water bath for complete solubilization. In the case of protein/peptide sequences including residues susceptible to oxidation, 0.25 mg N-acetyl-methionine (Ac-Met-OH) (191.25 g/mol) for 100 μl formulation mixture may be added as anti-oxidizing agent and the mixture was heated at 40-45° C. in a water bath till a limpid solution was obtained. The mixture has a pH of between 3.0 and 5.0 (typically around 3.5-4.0, depending on addition of Ac-Met-OH anti-oxidant, which is acidic), which could be adjusted by the addition of acid or base and/or buffered depending on the pI of the peptide, and was added to the peptide-crown complex.

In a particular case, Formulation 1a, the NMP can be substituted by 14 µl of propylene-glycol, or glycerol or a mixture of the two and the peptide complex forms in situ in the organic solvent. Then the vehicle comprising oleic acid (40 µl), nonanoic acid (50 µl) and decanoyl glycerol (130 mg) is added to the peptide complex in the polyol organic mixture.

Formulation 2:

The formulation vehicle was prepared by adding NMP (25 µl), Cremophor EL (35 µl) followed by nonanoic acid (50 µl) to decanoyl glycerol (130 mg). The obtained mixture was heated at 40-45° C. in a water bath for complete solubilization. In the case of peptide sequences including residues susceptible to oxidation, 0.25 mg Ac-Met-OH (191.25 g/mol) for 100 µl formulation mixture were then added as anti-oxidizing agent, and the mixture was heated at 40-45° C. in a water bath till a limpid solution was obtained. The mixture, without the peptide has a pH of between 4.0 and 6.0, which could be adjusted by the addition of acid or base and/or buffered depending on the pI of the peptide, and was added to the peptide-crown complex.

Formulation 3:

The formulation vehicle was prepared by adding octanoyl glycerol (50 mg), NMP (25 µl), and vitamin E (50 µl) to decanoyl glycerol (130 mg). The obtained mixture was heated at 40-45° C. in a water bath for complete solubilization. In the case of peptide sequences including residues susceptible to oxidation, 0.25 mg N-acetyl-methionine-amide (Ac-Met-NH$_2$) (190.27 g/mol) for 100 µl formulation mixture were then added as anti-oxidizing agent, and the mixture was heated at 40-45° C. in a water bath till a limpid solution was obtained. The mixture without the peptide has a pH estimated of between 5.5. and 7.0, which could be adjusted by the addition of acid or base and/or buffered depending on the pI of the peptide, and was added to the peptide-crown complex.

Formulation 4:

The formulation vehicle was prepared by adding a mixture of span 20 (60 µl) and oleic acid (50 µl) to decanoyl glycerol (110 mg). The obtained mixture was heated at about 45° C. in a water bath for complete solubilization. In this case, the peptide complex was obtained by dissolving the peptide in 14 µl propylene glycol containing the crown compound. After 15 nm at room temperature, the formulation vehicle was added to the peptide-crown complex in propylene glycol.

Formulation 5:

The formulation vehicle was prepared by adding a mixture of span 20 (60 µl), Monolinolein (mono acylglycerol of linoleic acid) (50 µl) and decanoyl glycerol (110 mg). The obtained mixture was heated at about 45° C. in a water bath for complete solubilization. In this case, the peptide complex was obtained by dissolving the peptide in 14 µl propylene glycol containing the crown compound. After 15 min at room temperature, the formulation vehicle was added to the peptide-crown complex in propylene glycol.

For the above non-aqueous hydrophobic vehicles (i.e., Formulations 1 to 5), one or more components may be eliminated or replaced by analogous compounds for other formulations. For example, other anti-oxidizing agents such as biotin, biotin ethyl ester or vitamin C can be used.

II. Test Articles

Mucosal delivery formulations containing parathyroid hormone, exendin-4, liraglutide, or human insulin were pre-screened for solubility, stability, and/or sublingual mucosal delivery in mice and/or rats using various crown compounds, counter ions, and non-aqueous hydrophobic vehicles in general. Representative crown compounds included 18-crown-6, oxo-(18-crown-6), oxo-(18-crown-6)-diethyl tartrate, and oxo-(18-crown-6)-diglycerol tartrate. Representative counter ions included TFA, acetate, salicylic acid, DLPG, $C_{12}H_{25}OSO_3H$, $C_{14}H_{29}SO_3H$, and $C_{18}H_{37}SO_3H$. Representative non-aqueous hydrophobic vehicles included vehicle Formulations 1, 2 and 3. All peptides were detected in the blood stream to different degrees.

Exendin-4 (having a calculated isoelectric point of about 5.0) was chosen for further detailed studies, which were carried out in accordance with the procedures and formulations described above in Experimental Section I unless otherwise indicated. Illustrative studies are reported below.

III. Animal Studies with Representative Mucosal Delivery Formulations

All mice or rats used in these studies were age- and sex-matched from the same litter or family for each individual study. All procedures were conducted according to approved protocols and guidelines following standard procedures. Studies for mice are detailed below, and are representative of the rat studies.

Intraperitoneal glucose tolerance tests (IPGTT) were carried out following an overnight fast (approximately 16-18 h). Mice were anesthetized at t=−40 minutes. At t=−30 minutes, test articles or saline control were administered sublingually (SubL) or by intraperitoneal administration (IP). At t=0 minutes, IP keta-xyla 100 µl IP glucose were administered. An additional 150 ul of anesthetics were administered as needed during an experiment. Anesthetized mice received either 5-10 nmols peptide of test article in a volume of 3-5 µl mucosal delivery formulation vehicle SubL, or 1 nmol of peptide control IP.

Blood samples were collected at various time points after treatment, and blood glucose levels determined by the glucose oxidase method following standard procedures. All animals remained anesthetized throughout blood collection. Changes in plasma glucose in mice were used to indicate the appearance of bioactive amounts of peptide test articles.

Test articles were stored at 4° C., and then warmed to 37° C. prior to administration. Data were analyzed and reported as mean±S.E.M. unless otherwise indicated.

Counter Ion

FIG. 1 shows the results obtained in mice for exendin-4 constructed with different counter ions in vehicle Formulation 1 (F1=acetate counter ion; F2=DLPG counter ion; F3=salicylic acid counter ion) with 18-crown-6 as the crown compound. It is noted that DLPG and salicylic acid (SA) are more acidic than acetic acid (DLPG pKa <2, SA pKa 2.97, and acetic acid pKa 4.76 in water).

For the data shown in FIG. 1, the following protocol was employed:

Step A. Preparation of Exendin-4 Salts:

(i) Acetate: 6 samples of 2.4 ml each containing 3.6 mg exendin-4 in the commercially available Byetta formulation (pH 4.5) were combined and freeze-dried. Obtained material was subjected to reverse phase high performance liquid chromatography (RP-HPLC) in water and acetonitrile in the presence of 1% acetic acid, followed by lyophilization. The lyophilized material was further purified using a SepPack C18 cartridge (elution of the peptide with water acetonitrile mixtures containing 1% acetic acid), affording pure exendin-4 used as-is or subjected to counter ion exchange in Step A(ii) or Step A(iii) below.

(ii) DLPG (610 g/mol, 0.66 mg): 0.66 mg DLPG (dilauryloylphosphatidylglycerol) was dissolved in 100 μl ACN/H$_2$O 50/50. This solution was added to 0.76 mg exendin-4 acetate in 50 μl ACN/H$_2$O 50/50, which was then subjected to concentration by speedvac for 1 hour at approximately 35° C. An additional aliquot of ACN/H$_2$O 50/50 was then added followed by drying by speedvac for 1 hour at approximately 35° C.

(iii) Salicylic acid (138.12 g/mol, 0.15 mg) 1.5 mg salicylic acid was dissolved in 100 μl ACN/H$_2$O 50/50 mixture to give the mother solution. 10 μl of this latter solution were then added to 0.76 mg exendin-4 acetate dissolved in 50 μl ACN/H$_2$O 50/50 followed by speedvac 2×1 hour as above at approximately 35° C., affording exendin-4 salicylate as a white solid.

Step B. Preparation of the Exendin-4 Salt-18-Crown-6 Complex:

Exendin-4 salts from step A were dissolved in MeOH (50 μl) and 10 mg 18-crown-6 in 100 μl MeOH were added followed by speedvac 1 hour at approximately 35° C. to yield an oily residue. Approximately 80 μl of the vehicle Formulation 1 was added to the exendin-4-crown complexes from Step A to obtain approximately 90 μl of formulations F1, F2 and F3, which were vortexed then heated at 40° C. for 10 minutes. The obtained preparations were then stored at +4° C. until use. For the animal study, the formulations were warmed to 37° C., and then 3 μl (approximately 6 nmols exendin-4 test article) of the F1, F2 and F3 mixtures were administered sublingually to mice.

The as-administered mucosal delivery composition of Table 1 (with data illustrated in FIG. 1): 208 stoichiometric equivalents of crown to peptide (i.e., approximately 35 crown molecules per basic amino group), 6 stoichiometric equivalents of counter ion to peptide (i.e., 1 counter ion molecule per basic amino group), resulting in a ratio of 35 crowns per 1 counter ion.

TABLE 1

Mucosal delivery compositions as administered (FIG. 1)

| Ref | Peptide | nmols | Crown | nmols | Counter Ion | nmols | Solubility |
|---|---|---|---|---|---|---|---|
| F1 | EX-4 | 6 | 18-cr-6 | 1250 | acetate | >36+ | pseudo limpid* |
| F2 | EX-4 | 6 | 18-cr-6 | 1250 | DLPG | 36 | limpid |
| F3 | EX-4 | 6 | 18-cr-6 | 1250 | salicylate | 36 | limpid |

All formulations contain 40 nmols Ac-Met-OH;
18-cr-6 = 18-crown-6;
+estimated;
*slight precipitate.

As illustrated in FIG. 1, salicylic counter ion exhibited the best activity.

Vehicle pH and Composition

Figure 2:
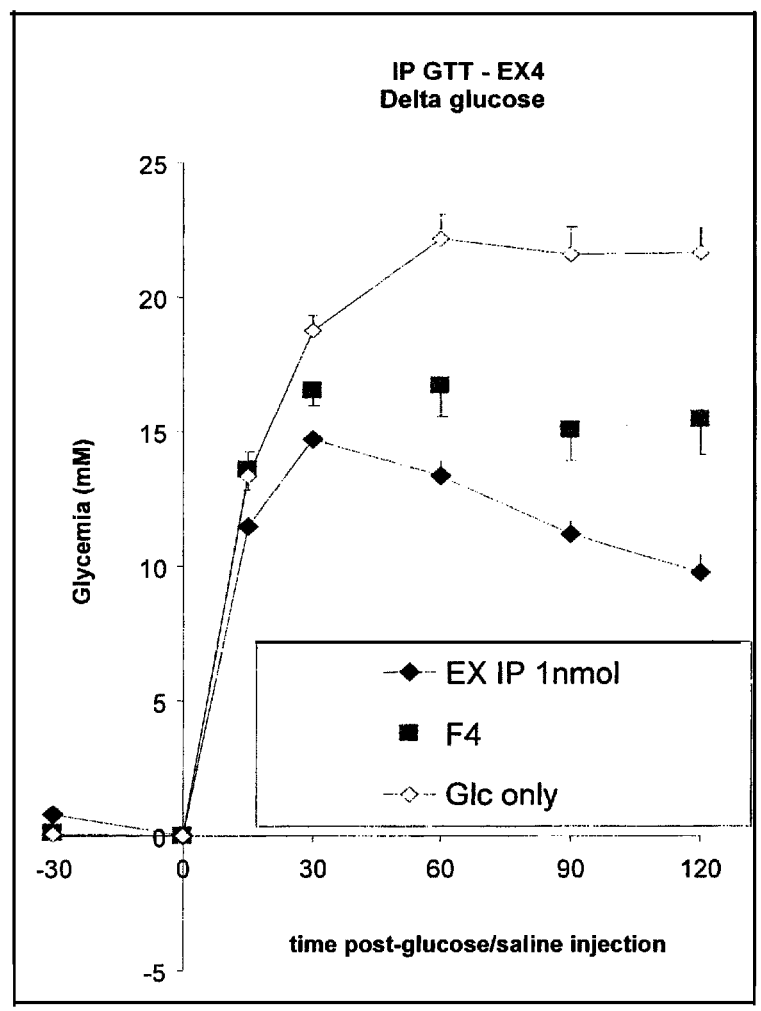
FIG. 2 depicts a set of results demonstrating the effect of altering vehicle pH on sublingual delivery of exendin-4 in a representative mucosal delivery composition, and reduction of glucose levels in mice as measured by IPGTT.

FIG. 2 shows the effect of altering the pH of the non-aqueous hydrophobic vehicle and composition on sublingual administration of exendin-4. FIG. 2 Key: F4=exendin-4 peptide with acetate counter ion and oxo-(18-crown-6)-diethyl tartrate ("ST5") crown compound formed in MeOH 100% and speedvac for 1 hour at approximately 35° C., followed by incorporation in Formulation 3. The as-administered mucosal delivery composition of Table 2 (with data illustrated in FIG. 2): 50 stoichiometric equivalents of crown to peptide (i.e., approximately 8 crown molecules per basic amino group), 12 stoichiometric equivalents of counter ion to peptide (i.e., 2 counter ion molecule per basic amino group), resulting in a ratio of 4 crowns per 1 counter ion.

TABLE 2

Mucosal delivery composition as administered (FIG. 2)

| Ref | Peptide | nmols | Crown | nmols | Counter Ion | nmols | Solubility |
|---|---|---|---|---|---|---|---|
| F4 | EX-4 | 5 | ST5 | 250 | acetate | 60 | limpid |

Formulation contains 40 nmols Ac-Met-OH

The results illustrated in FIG. 2 show that the exendin-4 peptide complex in vehicle Formulation 3 results in reduced sublingual delivery compared to when formulated in a more acidic vehicle such as Formulation 1, the latter also being further away from the pI of the peptide.

Also, studies comparing Formulations 1-3, as well as multiple others, reveal that Formulation 1 is suitable for exendin-4, exhibiting similar pharmacokinetics and about 20% pharmacological bioavailability relative to intrapleural administration when employing the biodegradable crown compound oxo-(18-crown-6)-diethyl tartrate and salicylic counter ion counter ion. Based on these studies, exendin-4 complexed with oxo-(18-crown-6)-diethyl tartrate and salicylic counter ion, and formulated in vehicle Formulation 1 were examined in greater detail. Representative results are reported in the following experiments.

Crown Compound and Counter Ion Molar Equivalents Per Basic Amino Group

Exendin-4 contains four primary amines (1 for N-terminus, 2 for the two lysines, and 1 for arginine), and two secondary amines (1 for histidine, and 1 for arginine), for a total of six basic amino groups ionizable under acidic conditions. The exendin-4 amino acid sequence is as follows:

(SEQ ID NO: 1)
HGEGTFTSDLSKQMEEEAVRLFIEWLKNGGPSSGAPPPS-NH$_2$

Figure 3:
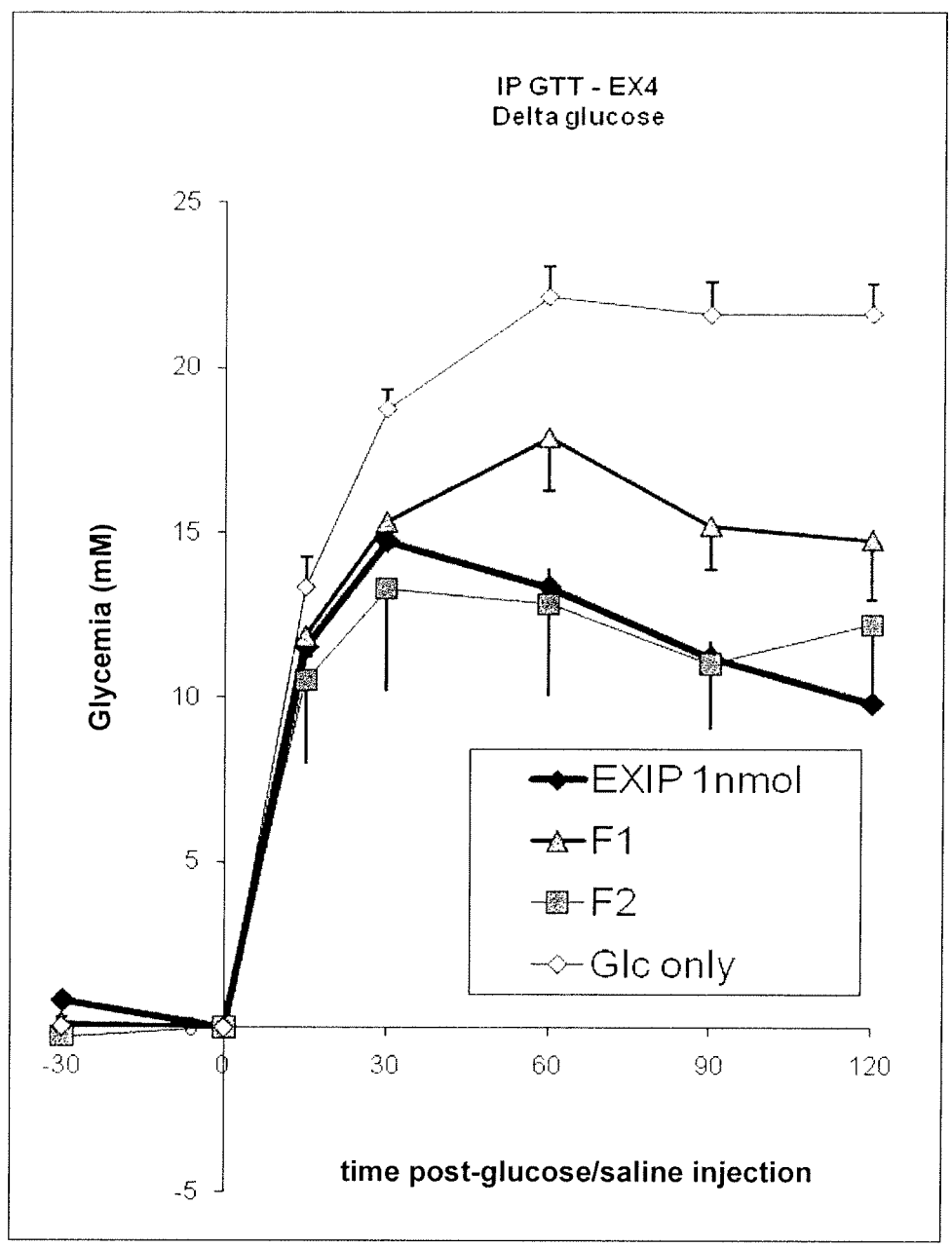
FIG. 3 depicts a set of results demonstrating the effect of altering the stoichiometric amounts and ratios of crown compound and counter ion to peptide on sublingual delivery of exendin-4 in representative mucosal delivery composition, and reduction of glucose levels in mice as measured by IPGTT.

FIG. 3 shows the results of adjusting stoichiometric equivalents of counter ion and crown compound (oxo-(18-crown-6) diethyl tartrate) on mucosal delivery in vehicle Formulation 1. A summary of the as-administered mucosal delivery composition is provided in Table 3. FIG. 3 Key: F1=exendin-4 with 24 stoichiometric equivalents of crown to peptide (i.e., 4 crown molecules per basic amino group), 6 stoichiometric equivalents of counter ion to peptide (i.e., 1 counter ion molecule per basic amino group), resulting in a ratio of 4 crowns per 1 counter ion. F2=exendin-4 with 12 stoichiometric equivalents of crown to peptide (i.e., 2 crown molecules per basic amino group), 6 stoichiometric equivalents of counter ion to peptide (i.e., 1 counter ion molecule per basic amino group), resulting in a ratio of 2 crowns per 1 counter ion. The results demonstrate the effect of crown compound and counter ion on mucosal delivery, with F2 exhibiting better performance.

TABLE 3

Mucosal delivery composition as administered (FIG. 3)

| Ref | Peptide | nmols | Crown | nmols | Counter Ion | nmols | Solubility |
|---|---|---|---|---|---|---|---|
| F1 | exendin-4 | 5 | ST5 | 120 | salicylate | 30 | limpid |

TABLE 3-continued

Mucosal delivery composition as administered (FIG. 3)

| Ref | Peptide | nmols | Crown | nmols | Counter Ion | nmols | Solubility |
|---|---|---|---|---|---|---|---|
| F2 | exendin-4 | 5 | ST5 | 60 | salicylate | 30 | limpid |

All formulations contain 40 nmols Ac-Met-OH

Water Content

Figure 4:
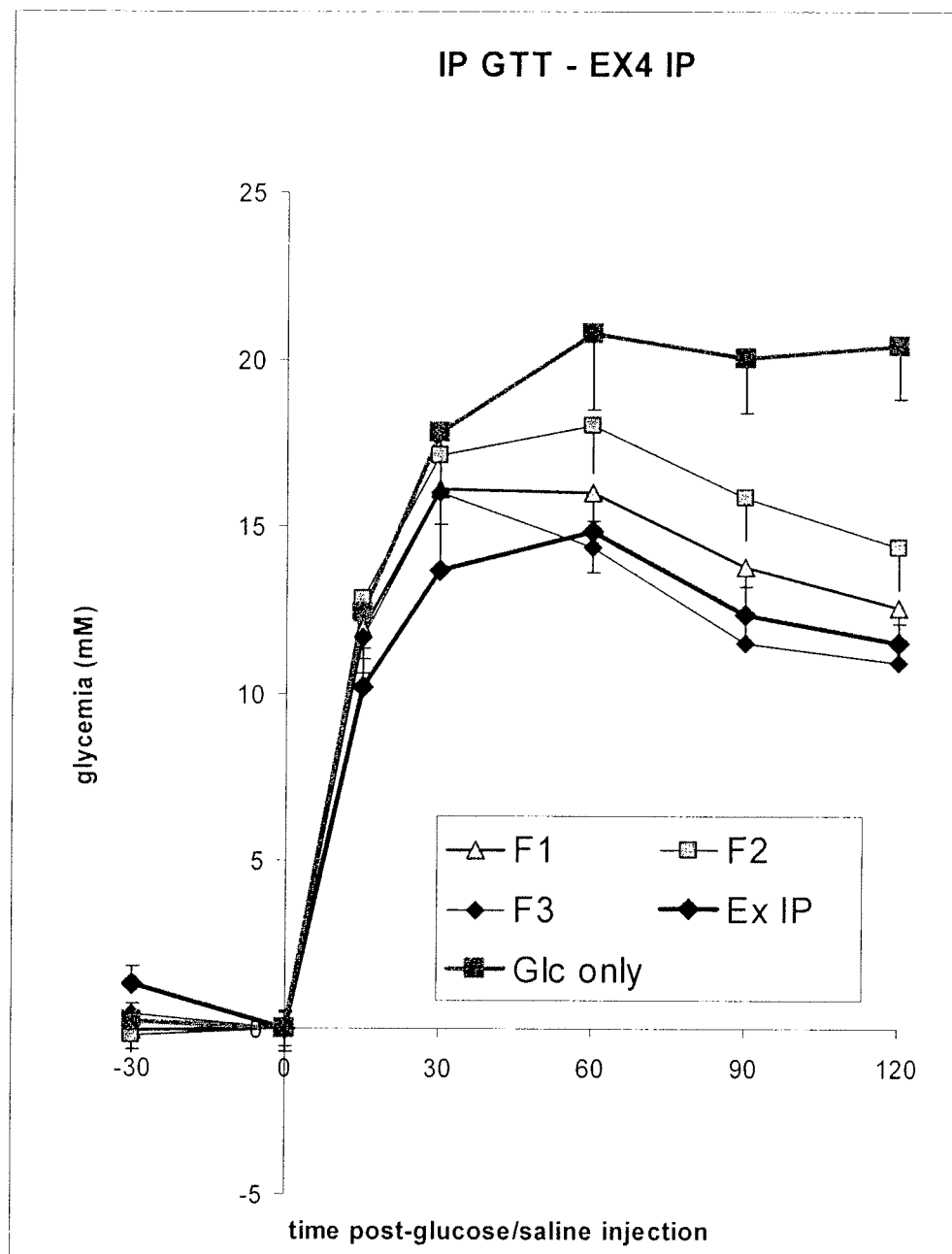
FIG. 4 depicts a set of results demonstrating the effect of water content and processing conditions on sublingual delivery of exendin-4 in a representative mucosal delivery composition, and reduction of glucose levels in mice as measured by IPGTT.

FIG. 4 shows the effect of water content on mucosal delivery of exendin-4. FIG. 4 Key: F1=exendin-4 peptide complex formed in MeOH 100% and speedvac for 1 hour at approximately 35° C., followed by incorporation in Formulation 1. F2=exendin-4 peptide complex formed in MeOH 100% and speedvac for 1 hour and 20 minutes at approximately 35° C., followed by incorporation in Formulation 1. F3=exendin-4 peptide complex formed in MeOH 5% water and speedvac for 1 hour at approximately 35° C., followed by incorporation in Formulation 1. The as-administered mucosal delivery composition of Table 4 (with data illustrated in FIG. 4): 12 stoichiometric equivalents of crown to peptide (i.e., approximately 2 crown molecules per basic amino group), 6 stoichiometric equivalents of counter ion to peptide (i.e., 1 counter ion molecule per basic amino group), resulting in a ratio of 2 crowns per 1 counter ion.

TABLE 4

Mucosal delivery composition as administered (FIG. 4)

| Ref | Peptide | nmols | Crown | nmols | Counter Ion | nmols | Solubility |
|---|---|---|---|---|---|---|---|
| F1 | EX-4 | 5 | ST5 | 60 | salicylate | 30 | limpid |
| F2 | EX-4 | 5 | ST5 | 60 | salicylate | 30 | limpid |
| F3 | EX-4 | 5 | ST5 | 60 | salicylate | 30 | limpid |

Vehicle Formulation 1 containing 40 nmols Ac-Met-OH

The data shows that reducing the water content by standard centrifugal evaporation or for longer times decreases biological activity compared to peptide complex formation in a mixed aqueous-methanol solution. Also, reducing the water content may alter the system pH and/or pI of the peptide active agent. Multiple additional data sets revealed similar results consistent with the finding that water content of the peptide and pH/pI of the system is important for activity, including improved solubility in organic solvent and the non-aqueous hydrophobic vehicle when the peptide and/or peptide complex is dried from a solution or suspension having a pH different, typically remote from the pI of the peptide.

In addition, the results demonstrate that selection of the crown compound, counter ion, amounts and ratios of crown to counter ion and ionizable amino groups of the peptide, as well as components and amounts thereof of the non-aqueous hydrophobic vehicle, inclusion of particular excipients, antioxidants and the like, can be exploited to improve or enhance mucosal delivery of peptides, among other aspects such as storage-stability and dosage form. In accordance with the fundamental nature of these findings, it is apparent that the compositions can be readily tailored for multiple different peptides and applications.

Although the foregoing disclosure has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the disclosure. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

The invention claimed is:

1. A mucosal delivery composition comprising an effective amount of a stably hydrated peptide active agent complexed with a crown compound and/or a counter ion solubilized in a non-aqueous hydrophobic vehicle at a pH different from the isoelectric point (pI) of the peptide active agent, wherein the non-aqueous hydrophobic vehicle is acidic or neutral and comprises (a) at least one medium chain acylglycerol, (b) at least one polar organic solvent and (c) at least one lipid, wherein the non-aqueous hydrophobic vehicle is effective to (i) solubilize the stably hydrated peptide active agent complexed with the crown compound and/or the counter ion, and (ii) enhance mucosal delivery of the peptide active agent.

2. The mucosal delivery composition of claim 1, wherein the stably hydrated peptide active agent has a water content of about 1% to about 50% by weight.

3. The mucosal delivery composition of claim 1, wherein the pH differs by about 0.5 to about 4 pH units from the pI of the peptide active agent.

4. The mucosal delivery composition of claim 1, wherein the stably hydrated peptide active agent complexed with the crown compound and/or the counter ion is preformed as a dried peptide from a solution or suspension having a pH different from the pI of the peptide active agent.

5. The mucosal delivery composition of claim 1, wherein the at least one polar organic solvent is an alcohol, or a polar aprotic solvent.

6. The mucosal delivery composition of claim 5, wherein the alcohol is ethanol.

7. The mucosal delivery composition of claim 4, wherein the solution or suspension comprises an aqueous methanol solution or suspension having a water content of about 1% to about 20%, or an aqueous acetonitrile solution or suspension having a water content of about 30% to about 70%.

8. The mucosal delivery composition of claim 4, wherein the preformed dried peptide is storage stable.

9. The mucosal delivery composition of claim 1, wherein the composition is storage stable.

10. The mucosal delivery composition of claim 1, wherein the peptide active agent upon sublingual administration of the composition has a pharmacological bioavailability of greater than about 10% relative to intrapleural administration.

11. The mucosal delivery composition of claim 1, wherein the peptide active agent comprises one or more cationic groups, the crown compound is a cation-binding crown compound, and the counter ion is an anionic counter ion.

12. The mucosal delivery composition of claim 11, wherein the one or more cationic groups is selected from the group consisting of a primary amine, a secondary amine, a guanidinium group, and combinations thereof.

13. The mucosal delivery composition of claim 12, wherein the cation-binding crown compound and the anionic counter ion are each individually present at about 0.5 to 10 stoichiometric equivalents per primary amine, secondary amine, and/or guanidinium group.

14. The mucosal delivery composition of claim 13, wherein the cation-binding crown compound is present at about 2 to 4 stoichiometric equivalents per primary amine, secondary amine, and/or guanidinium group.

15. The mucosal delivery composition of claim 13, wherein the cationic counter ion is present at about 1 to 2 stoichiometric equivalents per primary amine, secondary amine, and/or guanidinium group.

16. The mucosal delivery composition of claim 13, wherein the cation-binding crown compound is present at about 2 stoichiometric equivalents per primary amine, secondary amine, and/or guanidinium group, and the cationic counter ion is present at about 1 stoichiometric equivalents per primary amine, secondary amine, and/or guanidinium group.

17. The mucosal delivery composition of claim 1, wherein the crown compound comprises a biodegradable linkage.

18. The mucosal delivery composition of claim 17, wherein the biodegradable linkage is an ester linkage.

19. The mucosal delivery composition of claim 18, wherein the crown compound is selected from the group consisting of oxo-(18-crown-6) compounds and analogs/derivatives thereof.

20. The mucosal delivery composition of claim 19, wherein the crown compound is selected from the group consisting of oxo-(18-crown-6), oxo-(18-crown-6)-diethyl tartrate, and oxo-(18-crown-6)-diglycerol tartrate.

21. The mucosal delivery composition of claim 1, wherein the counter ion is selected from the group consisting of salicylic acid, acetic acid, phosphoric acid, tartaric acid, N-acetyl-lysine-amide, N-acetyl-arginine-amide, benzoic acid and analogs/derivatives thereof, oxalic acid, sulfonates, sulfates, phosphatidylglycerol derivatives, phosphoric acid, trifluoroacetic acid, chloride, and mixtures thereof.

22. The mucosal delivery composition of claim 1, wherein the composition comprises a pharmaceutically acceptable excipient selected from the group consisting of buffer, preservative, isotonic agent, and an antioxidant.

23. The mucosal delivery composition of claim 1, wherein the at least one polar organic solvent is a water soluble organic solvent.

24. The mucosal delivery composition of claim 23, wherein the non-aqueous hydrophobic vehicle is acidic, and wherein the at least one lipid comprises a short chain fatty acid and/or a medium chain fatty acid, and the water soluble organic solvent is a polar aprotic solvent.

25. The mucosal delivery composition of claim 24, wherein the medium chain acylglycerol is mono-decanoyl glycerol, the short chain fatty acid is nonanoic acid, the medium chain fatty acid is oleic acid, and the polar aprotic solvent is N-methyl-2-pyrrolidone.

26. The mucosal delivery composition of claim 23, wherein the non-aqueous hydrophobic vehicle is neutral, and wherein at least one acylglycerol is a medium chain acylglycerol, at least one lipid is a neutral lipid, and the water soluble organic solvent is a polar aprotic solvent.

27. The mucosal delivery composition of claim 26, wherein the medium chain acylglycerol is mono-decanoyl glycerol, octanoyl glycerol, or a mixture thereof, the neutral lipid is vitamin E, and the water soluble organic solvent is N-methyl-2-pyrrolidone.

28. The mucosal delivery composition of claim 22, wherein the antioxidant is selected from the group consisting of N-acetyl-methionine, biotin, biotin ethyl ester, and ascorbic acid.

29. The mucosal delivery composition of claim 1, wherein the peptide active agent is a peptide hormone.

30. The mucosal delivery composition of claim 29, wherein the peptide hormone is a glucagon-like peptide, and analogs/derivatives thereof.

31. The mucosal delivery composition of claim 30, wherein the glucagon-like peptide is selected from the group consisting of glucagon-like peptide 1, exenatide, liraglutide, and analogs/derivatives thereof.

32. The mucosal delivery composition of claim 1, wherein the mucosal delivery composition comprises a dosage form selected from the group consisting of buccal, sublingual, and a combination thereof.

33. The mucosal delivery composition of claim 1, wherein the composition is a micelle.

34. The mucosal delivery composition of claim 1, wherein the micelle is a reverse micelle.

35. A method of producing a mucosal delivery composition for use in mucosal delivery of a peptide active agent into the bloodstream of a host, the method comprising:
  forming a stably hydrated peptide active agent complex comprising a peptide active agent and a crown compound and/or a counter ion solubilized in a non-aqueous hydrophobic vehicle at a pH different from the isoelectric point (pI) of the peptide active agent, wherein the non-aqueous hydrophobic vehicle is acidic or neutral and comprises (a) at least one medium chain acylglycerol, (b) at least one polar organic solvent and (c) at least one lipid, wherein the non-aqueous hydrophobic vehicle is effective to (i) solubilize the stably hydrated peptide active agent complexed with the crown compound and/or the counter ion, and (ii) enhance mucosal delivery of the peptide active agent.

36. The method of claim 35, wherein said forming comprises combining an effective amount of (i) the non-aqueous hydrophobic vehicle, and (ii) the peptide active agent complex.

37. The method of claim 36, wherein the peptide active agent complex is a dry powder or residue obtainable by drying an aqueous organic solution or suspension, the aqueous organic solution or suspension comprising as components therein the peptide active agent, the crown compound, and the counter ion, and wherein the drying is under conditions that retain a sufficient amount of water in association with the peptide active agent to produce the peptide complex.

38. The method of claim 35, wherein the peptide active agent and the counter ion are preformed as a peptide salt.

39. The method of claim 38, wherein the peptide salt is a dry powder or residue obtainable by drying a solution or suspension comprising as components therein the peptide active agent and the counter ion.

40. The method of claim 35, wherein said forming comprises combining an effective amount of (i) a non-aqueous hydrophobic vehicle having an effective amount of a stably hydrated peptide active agent complexed with a counter ion, and (ii) a crown compound.

41. The method of claim 40, wherein the peptide active agent complexed with the counter ion is preformed as a peptide salt.

42. The method of claim 41, wherein the peptide salt is a dry powder or residue obtainable by drying a solution or suspension comprising as components therein the peptide active agent and the counter ion.

43. A method of mucosal delivery of an effective amount of a peptide active agent to a host in need thereof, the method comprising:
  administering to a mucosal membrane of the host an effective amount of a mucosal delivery composition according to claim 1, wherein the administering delivers an effective amount of the peptide active agent into the blood stream of the host.

44. The method of claim 43, wherein the mucosal membrane is an oral mucosal membrane.

45. The method of claim 44, wherein the oral mucosal membrane is selected from the group consisting of buccal, sublingual, and combinations thereof.

46. The method of claim 45, wherein the sublingual administration of the composition results in a pharmacological bioavailability of the peptide active agent that is greater than about 10% relative to intrapleural administration.

47. A preformed peptide complex comprising a stably hydrated peptide active agent complexed with a crown compound and a counter ion, wherein the preformed peptide complex, dried from a solution or suspension, is in a non-aqueous hydrophobic vehicle at a pH different from the isoelectric point (pI) of the peptide active agent, wherein the non-aqueous hydrophobic vehicle is acidic or neutral and comprises (a) at least one medium chain acylglycerol, (b) at least one polar organic solvent and (c) at least one lipid, wherein the non-aqueous hydrophobic vehicle is effective to (i) solubilize the stably hydrated peptide active agent complexed with the crown compound and the counter ion, and (ii) enhance mucosal delivery of the peptide active agent.

48. The preformed peptide complex of claim 47, wherein the organic solvent is an alcohol, or a polar aprotic solvent.

49. The preformed peptide complex of claim 48, wherein the alcohol is ethanol.

50. The preformed peptide complex of claim 47, wherein the preformed peptide complex has a shelf life equal or greater than one month when stored at a temperature in the range of −20° C. to 25° C.

51. A kit for use in mucosal delivery of a peptide active agent into the bloodstream of a host, the kit comprising an effective amount of a mucosal delivery composition according to claim 1, and/or components thereof in a combination capable of forming the mucosal delivery composition.

52. The mucosal delivery composition of claim 21, wherein the sulfate is lauryl sulfate.

53. The mucosal delivery composition of claim 21, wherein the phosphatidylglycerol derivatives is dilauryl-phosphatidyl glycerol.

54. The mucosal delivery composition of claim 4, wherein the pH difference is greater than about 0.5 pH units from the pI of the peptide active agent.

55. The mucosal delivery composition of claim 4, wherein the pH difference is greater than about 0.9 units from the pI of the peptide active agent.

56. The mucosal delivery composition of claim 4, wherein the pH difference is greater than about 1.0 pH units from the pI of the peptide active agent.

57. The mucosal delivery composition of claim 4, wherein the pH difference is greater than about 1.5 pH units from the pI of the peptide active agent.

* * * * *